(12) United States Patent
Zitvogel et al.

(10) Patent No.: US 10,765,710 B2
(45) Date of Patent: Sep. 8, 2020

(54) COMBINATION OF ONCOLYTIC VIRUS WITH IMMUNE CHECKPOINT MODULATORS

(71) Applicants: Institut Gustave-Roussy, Villejuif (FR); Transgene SA, Illkirch Graffenstaden (FR)

(72) Inventors: Laurence Zitvogel, Paris (FR); Xavier Preville, Saint Louis (FR); Laetitia Fend, Le Kremlin-bicetre (FR)

(73) Assignees: Institut Gustave-Roussy, Villejuif (FR); Transgene SA, Illkirch Graffenstaden (FR)

( * ) Notice: Subject to any disclaimer, the term of this patent is extended or adjusted under 35 U.S.C. 154(b) by 0 days.

(21) Appl. No.: 15/325,576

(22) PCT Filed: Jul. 16, 2015

(86) PCT No.: PCT/EP2015/066353
§ 371 (c)(1),
(2) Date: Jan. 11, 2017

(87) PCT Pub. No.: WO2016/009017
PCT Pub. Date: Jan. 21, 2016

(65) Prior Publication Data
US 2017/0143780 A1 May 25, 2017

(30) Foreign Application Priority Data
Jul. 16, 2014 (EP) ..................................... 14306155

(51) Int. Cl.
| | | |
|---|---|---|
| *A61K 35/768* | (2015.01) | |
| *A61K 35/28* | (2015.01) | |
| *C07K 16/20* | (2006.01) | |
| *C07K 16/30* | (2006.01) | |
| *C12N 5/00* | (2006.01) | |
| *A61K 9/00* | (2006.01) | |
| *A61K 38/19* | (2006.01) | |
| *A61K 39/395* | (2006.01) | |
| *C07K 16/28* | (2006.01) | |
| *C12N 7/00* | (2006.01) | |
| *A61K 39/00* | (2006.01) | |

(52) U.S. Cl.
CPC .......... *A61K 35/768* (2013.01); *A61K 9/0019* (2013.01); *A61K 35/28* (2013.01); *A61K 38/193* (2013.01); *A61K 39/3955* (2013.01); *C07K 16/2818* (2013.01); *C07K 16/2827* (2013.01); *C12N 5/00* (2013.01); *C12N 7/00* (2013.01); *A61K 2039/505* (2013.01); *C07K 2317/76* (2013.01); *C12N 2710/24132* (2013.01)

(58) Field of Classification Search
CPC ..... A61K 35/768; A61K 35/28; A61K 9/0019

USPC ............................................ 424/133.1, 178.1
See application file for complete search history.

(56) References Cited

U.S. PATENT DOCUMENTS

| | | | |
|---|---|---|---|
| 5,225,539 A | 7/1993 | Winter | |
| 5,457,035 A | 10/1995 | Baum et al. | |
| 5,530,101 A | 6/1996 | Queen et al. | |
| 5,773,578 A | 6/1998 | Hercend et al. | |
| 6,180,370 B1 | 1/2001 | Queen et al. | |
| 6,984,720 B1 | 1/2006 | Korman et al. | |
| 7,109,003 B2 | 9/2006 | Hanson et al. | |
| 7,291,331 B1 | 11/2007 | Croft et al. | |
| 7,410,644 B2 | 8/2008 | Schlom et al. | |
| 7,622,444 B2 | 11/2009 | Weinberg | |
| 8,017,114 B2 | 9/2011 | Korman et al. | |
| 8,143,379 B2 | 3/2012 | Hanson et al. | |
| 8,491,895 B2 | 7/2013 | Hanson et al. | |
| 2014/0140959 A1* | 5/2014 | Szalay | A61K 49/006 424/93.2 |
| 2016/0271239 A1* | 9/2016 | Foy | A61K 39/0011 |
| 2017/0106065 A1* | 4/2017 | Foy | A61K 39/0011 |
| 2017/0157188 A1* | 6/2017 | Silvestre | A61K 35/768 |
| 2017/0266270 A1* | 9/2017 | Foy | A61K 39/0011 |
| 2018/0028626 A1* | 2/2018 | Slos | A61K 39/0011 |
| 2018/0078591 A1* | 3/2018 | Deng | A61K 35/768 |

FOREIGN PATENT DOCUMENTS

| | | |
|---|---|---|
| IT | 1 907 000 B1 | 4/2008 |
| WO | WO 97/20574 | 6/1997 |
| WO | WO 03/045197 | 6/2003 |
| WO | WO 03/082919 | 10/2003 |
| WO | WO 03/106498 | 12/2003 |
| WO | WO 2004/004771 | 1/2004 |
| WO | WO 2004/056875 | 7/2004 |
| WO | WO 2006/121168 | 11/2006 |

(Continued)

OTHER PUBLICATIONS

Rojas et al (Clin Cancer Res. Dec. 15, 2015; 21(24): 5543-5551).*

(Continued)

*Primary Examiner* — Lynn A Bristol
(74) *Attorney, Agent, or Firm* — Panitch Schwarze Belisario & Nadel LLP

(57) ABSTRACT

The present invention provides a combination comprising at least an oncolytic virus and one or more immune checkpoint modulator(s) for use for the treatment of a proliferative disease such as cancer. It also relates to a kit comprising an oncolytic virus and one or more immune checkpoint modulator(s) in separate containers. It also concerns a pharmaceutical composition comprising effective amount of an oncolytic virus and one or more immune checkpoint modulator(s).

14 Claims, 6 Drawing Sheets

(56) References Cited

FOREIGN PATENT DOCUMENTS

| | | |
|---|---|---|
| WO | WO 2007/123737 | 11/2007 |
| WO | WO 2008/113078 | 9/2008 |
| WO | WO 2008/156712 | 12/2008 |
| WO | WO 2009/014708 | 1/2009 |
| WO | WO 2009/065546 | 5/2009 |
| WO | WO 2009/065547 | 5/2009 |
| WO | WO 2009/114335 | 9/2009 |
| WO | WO 2010/014784 | 2/2010 |
| WO | WO 2012/110360 | 8/2012 |
| WO | WO 2013/043569 | 3/2013 |
| WO | WO 2014/022138 | 2/2014 |
| WO | WO 2014/047350 | 3/2014 |

OTHER PUBLICATIONS

Zamarin et al. (Molecular Therapy—Oncolytics (2014) 1, 14004; published online Dec. 10, 2014).*
Dias et al. (2010) Clin. Canc. Res., vol. 16(9), 2540-2549.*
Fend et al. (Cancer Res; 77(15) Aug. 1, 2017: 4146-4257).*
Remy-Ziller (Human Vaccines & Immunotherapeutics 2018, vol. 14, No. 1, 140-145).*
Buijs et al. (Hum Vaccin Innnnunother. 2015;11(7):1573-84).*
Berenbaum Clin. Exp. Immunol. 28:1-18 (1977).*
Berenbaum Pharmacol. Rev. 41:93-141 (1989)).*
Tallarida "Drug Synergism and Dose Effect Analysis" Ed. Chapman & Hall (2000), pp. 1-71.).*
Merrick et al. (Curr Opin Investig Drugs. Dec. 2009;10(12):1372-82).*
Beaud Biochemie 77:774-779 (1995)).*
Agata et al., *Expression of the PD-1 antigen on the surface of stimulated mouse T and B lymphocytes*, 8(5) International Immunology 765-772 (1996).
Andtbacka et al., *OPTiM:A randomized phase III trial of talimogene laherparepvec (T-VEC) versus subcutaneous (SC) granulocyte-macrophage colony-stimulating factor (GM-CSF) for the treatment (tx) of unresected stage IIIB/C and IV melanoma*, 31 J. Clin Oncol 1-2 (2013).
Bedke et al., *Targeted therapy in renal cell carcinoma: moving from molecular agents to specific immunotherapy*, 32 World J. Urol. 31-38 (2014).
Bennett et al., *Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses*, 170 J. Immunol 711-718 (2003).
Blank et al., *Interaction of PD-L1 on tumor cells with PD-1 on tumor-specific T cells as a mechanism of immune evasion: implications for tumor immunotherapy*, 54 Cancer Immunol Immunother 307-314 (2005).
Blank et al., *The perspective of immunotherapy: new molecules and new mechanisms of action in immune modulation*, 26(2) Current Opin. Oncol. 204-214 (2014).
Boviatsis et al., *Antitumor activity and reporter gene transfer into rat brain neoplasms inoculated with herpes simplex virus vectors defective in thymidine kinase or ribonucleotide reductase*, 1(5) Gene Therapy 323-331 (Sep. 1994).
Breitbach et al., *Targeted and Armed Oncolytic Poxvirus for Cancer: the Lead Example of JX-594*, 13 Current Pharmaceutical Biotechnology 1768-1772 (2012).
Brunet et al., *A new member of the immunoglobulin superfamily—CTLA-4*, 328 Nature 267-270 (Jul. 16, 1987).
Champiat et al., *Incorporating Immune-Checkpoint Inhibitors into Systemic Therapy of NSCLC*, 9(2) Journal of Thoracic Oncology 144-153 (Feb. 2014).
Carter et al., *PD-1:PD-L inhibitory pathway affects both $CD4^+$ and $CD8^+$ T cells and is overcome by IL-2*, 32 Eur. J. Immunol 634-643 (2002).
Chambers et al., *Comparison of genetically engineered herpes simplex viruses for the treatment of brain tumors in a scid mouse model of human malignant glioma*, 92 Proc. Natl. Acad. Sci 1411-1415 (Feb. 1995).

Chernajovsky et al., *Fighting cancer with oncolytic viruses*, 332 BMJ 170-172 (Jan. 21, 2006).
Cohen et al., *ONYX-015 Onyx Pharmaceuticals*, 2(12) Current Opinion in Investigational Drugs 1770-1775 (2001).
Dariavach et al., *Human Ig superfamily CTLA-4 gene: chromosomal localization and identity of protein sequence between murine and human CTLA-4 cytoplasmic domains*, 18 Eur. J. Immunol. 1901-1905 (1988).
Dong et al., *B7-H1 pathway and its role in the evasion of tumor immunity*, 81 J. Mol Med 281-287 (2003).
Dong et al., *Tumor-associated B7-H1 promotes T-cell apoptosis: A potential mechanism of immune evasion*, 8(8) Nature Medicine 793-800 (Aug. 2002).
Engeland et al., *Measles Virus Mediated Immune Checkpoint Blockade Enhances Cancer Immunovirotherapy*, 22(Supplement 1) Molecular Therapy (May 2014) (abstract only).
Foloppe et al., *Targeted delivery of a suicide gene to human colorectal tumors by a conditionally replicating vaccinia virus*, 15 Gene Therapy 1361-1371 (2008).
Freeman et al., *Engagement of the PD-1 Immunoinhibitory Receptor by a Novel B7 Family Member Leads to Negative Regulation of Lymphocyte Activation*, 192(7) J. Exp. Med. 1027-1034 (Oct. 2, 2000).
Freeman et al., *Phase I/II Trial of Intravenous NDV-HUJ Oncolytic Virus in Recurrent Glioblastoma Multiforme*, 13(1) Molecular Therapy 221-228 (January 2006).
Gammon et al., *Vaccinia Virus-Encoded Ribonucleotide Reductase Subunits are Differentially Required for Replication and Pathogenesis*, 6(7) PLoS Pathogens 1-20 (Jul. 2010).
Geevarghese et al., *Phase I/II Study of Oncolytic Herpes Simplex Virus NV1020 in Patients with Extensively Pretreated Refractory Colorectal Cancer Metastatic to the Liver*, 21 Human Gene Therapy 1119-1128 (Sep. 2010).
Guse et al., *Oncolytic vaccinia virus for the treatment of cancer*, 11(3) Expert Opin. Biol. Ther. 595-608 (2011).
Hermiston, T., *A demand for next-generation oncolytic adenovirus*, 8(4) Current Opinion in Molecular Therapeutics 322-330 (Aug. 2006).
Kaufmann et al., *Chemovirotherapy of Malignant Melanoma with a Targeted and Armed Oncoytic Measles Virus*, 133 Journal of Investigative Dermatology 1034-1042 (2013).
Khuri et al., *A controlled trial of intratumoral ONYX-015, a selectively-replicating adenovirus, in combination with cisplatin and 5-fluorouracil in patients with recurrent head and neck cancer*, 6(8) Nature Medicine 879-885 (Aug. 2000).
Kirn et al., *Replication-selective virotherapy for cancer: Biological principles, risk management and future directions*, 7(7) Nature Medicine 781-787 (Jul. 2001).
Kirn et al., *Targeted and armed oncolytic poxviruses: a novel multi-mechanistic therapeutic class for cancer*, 9 Nature 64-71 (Jan. 2009).
Leach et al., *Enhancement of Antitumor Immunity by CTLA-4 Blockade*, 271 Science 1734-1736 (Mar. 22, 1996).
Lorence et al., *Phase 1 Clinical Experience Using Intravenous Administration of PV701, an Oncolytic Newcastle Disease Virus*, 7 Current Cancer Drug Targets 157-167 (2007).
Martuza et al., *Experimental Therapy of Human Glioma by Means of a Genetically Engineered Virus Mutant*, 252 Science 854-856 (Oct. 3, 1990).
McDonald et al., *A measles virus vaccine strain derivative as a novel oncolytic agent against breast cancer*, 99 Breast Cancer Research and Treatment 177-184 (2006).
Mineta et al, *Treatment of Malignant Gliomas Using Ganciclovir-hypersensitive, Ribonucleotide Reductase-deficient Herpes Simplex Viral Mutant*, 54 Cancer Research 3963-3966 (Aug. 1, 1994).
Okazaki et al., *New regulatory co-receptors: inducible co-stimulator and PD-1*, 14 Current Opinion in Immunology 779-782 (2002).
Phuangsab et al., *Newcastle disease virus therapy of human tumor xenografts: antitumor effects of local or systemic administration*, 172 Cancer Letters 27-36 (2001).

(56) References Cited

OTHER PUBLICATIONS

Presta et al., *Humanization of an Anti-Vascular Endothelial Growth Factor Monoclonal Antibody for the Therapy of Solid Tumors and Other Disorders*, 57 Cancer Research 4593-4599 (Oct. 15, 1997).
Pyles et al., *Evidence that the Herpes Simplex Virus Type 1 Uracil DNA Glycosylase is Required for Efficient Viral Replication and Latency in the Murine Nervous System*, 68(8) Journal of Virology 4963-4972 (Aug. 1994).
Qureshi et al., *Trans-endocytosis of CD80 and CD86: a molecular basis for the cell extrinsic function of CTLA-4*, 332(6029) Science 600-603 (2011).
Rudin et al., *Phase I Clinical Study of Seneca Valley Virus (SVV-001), a Replication-Competent Picornavirus, in Advanced Solid Tumors with Neuroendocrine Features*, 17(4) Clin Cancer Res 888-895 (Feb. 15, 2011).
Senzer et al., *Phase II Clinical Trial of a Granulocyte-Macrophage Colony-Stimulating Factor-Encoding, Second-Generation Oncolytic Herpesvirus in Patients With Unresectable Metastatic Melanoma*, 27(34) Journal of Clinical Oncology 5763-5771 (Dec. 1, 2009).
Stojdl et al., *Exploiting tumor-specific defects in the interferon pathway with a previously unknown oncolytic virus*, 6(7) Nature Medicine 821-825 (Jul. 2000).
Stojdl et al., *VSV strains with defects in their ability to shutdown innate immunity are potent systemic anti-cancer agents*, 4 Cancer Cell 263-275 (2003).
Thorne, *Immunotherapeutic potential of oncolytic vaccinia virus*, 4(Article 155) Frontiers in Oncology 1-5 (Jun. 2014).
Thorne et al., *Rational strain selection and engineering creates a broad-spectrum, systemically effective oncolytic poxvirus, JX-963*, 117(11) The Journal of Clinical Investigation 3350-3358 (Nov. 2007).
Topalian et al., *Targeting the PD-1/B7-H1(PD-L1) pathway to activate anti-tumor immunity*, 24(2) Curr. Opin. Immunol. 207-212 (Apr. 2012).
Wong et al., *Oncolytic Viruses for Cancer Therapy: Overcoming the Obstacles*, 2 Viruses 78-106 (2010).
Xia, et al., *Phase III randomized clinical trial on intratumoral injection of E1B gene-deleted adenovirus (H101) combined with cispliatin-based chemotherapy in treating squamous cell cancer of head and neck or esophagus*, 23(12) Ai Zheng 1666-1670 (Dec. 2004) (abstract only).
Zhang et al., *Eradication of Solid Human Breast Tumors in Nude Mice with an Intravenously Injected Light-Emitting Oncolytic Vaccinia Virus*, 67(20) Cancer Research 10038-10046 (Oct. 15, 2007).
International Search Report dated Sep. 21, 2015, and Written Opinion in corresponding PCT Application No. PCT/EP2015/066353.
Gomella et al., *Phase I study of intravesical vaccinia virus as a vector for gene therapy of bladder cancer*, 166(4) Journal of Urology 1291-1295 (Oct. 2001) (abstract only).
*Study of Pembrolizumab (MK-3475) in Participants With Advanced Solid Tumors (MK-3475-028/KEYNOTE-28)*, (First Posted Feb. 4, 2014) (https://clinicaltrials.gov/ct2/show/NCT02054806?term=MK-3475&rank=43) (Jul. 24, 2019).
*A Phase 1/2 Study Exploring the Safety, Tolerability, and Efficacy of Pembrolizumab (MK-3475) in Combination with Epacadostat (INCB024360) in Subjects With Selected Cancers (INCB 24360-202 / MK-3475-037 / KEYNOTE-037/ ECHO-202)* (First Posted Jul. 1, 2014) (https://clinicaltrials.gov/ct2/show/NCT02178722?term=MK-3475&rank=29) (Jul. 24, 2019).
*CT-011 and p53 Genetic Vaccine for Advanced Solid Tumors*, (First Posted Jul. 1, 2011) (https://clinicaltrials.gov/ct2/show/NCT01386502?term=CT-011&cond=cancer&rank=4) (Jul. 24, 2019).
*Anti PD1 Antibody in Diffuse Intrinsic Pontine Glioma*, (First Posted Sep. 30, 2013) (https://clinicaltrials.gov/ct2/show/NCT01952769?term=%28anti-PD1%29+or+%28anti-PD-1%29&cond=glioma&rank=1) (Jul. 24, 2019).
*Safety Study of Recombinant Vaccinia Virus to Treat Refractory Solid Tumors in Pediatric Patients*, (First Posted Jul. 26, 2010) (https://clinicaltrials.gov/ct2/show/NCT01169584) (Jul. 24, 2019).

*SARC028: A Phase II Study of the Anti-PD1 Antibody Pembrolizumab (MK-3475) in Patients with Advanced Sarcomas*, (First Posted Nov. 25, 2014) (https://clinicaltrials.gov/ct2/show/NCT02301039?term=anti-PD1+or+anti-PD-1&cond=bone+cancer&ranks=3) (Jul. 24, 2019).
Camacho et al., *A multi-targeted approach to treating bone metastases*, 33 Cancer Metastasis Rev. 545-553 (Online Jan. 4, 2014).
Chan et al., *Oncolytic Poxviruses*, 1(1) Ann Rev Virol., 119-141 (2014).
Berghoff et al., *PD1 (CD279) and PD-L1 (CD274, B7H1) expression in primary central nervous system lymphomas (PCNSL)*, 33(1) Clinical Neuropathology, 42-49 (online Dec. 20, 2013).
Finnefrock et al., *PD-1 Blockade in Rhesus Macaques: Impact on Chronic Infection and Prophylactic Vaccination*, 182 J. Immunol 980-987 (2009).
Gholami et al., *Novel therapy for anaplastic thyroid carcinoma cells using an oncolytic vaccinia virus carrying the human sodium iodide symporter*, 150(6) Surgery, 1040-1047 (2011).
He et al., *Effective Oncolytic Vaccinia Therapy for Human Sarcomas*, 175(2) J Surg Res. e53-e60 (2012).
Hui et al., *Phase I Trial of Recombinant Modified Vaccinia Ankara Encoding Epstein-Barr Viral Tumor Antigens in Nasopharyngeal Carcinoma Patients*, 73(6) Cancer Res. 1676-1688 (2013).
Lin et al., *Oncolytic Vaccinia Virotherapy of Anaplastic Thyroid Cancer in Vivo*, 93(111) J Clin Endocrinol Metab. 4403-4407 (2008).
Liu et al., *Oncolytic Vaccinia Virotherapy for Endometrial Cancer*, 132(3) Gynecol Oncol. 722-729 (Mar. 2014).
Lun et al., *Double-deleted vaccinia virus in virotherapy for refractory and metastatic pediatric solid tumors*, 7 Molecular Oncology, 944-954 (2013).
Qui et al., *Programmed death-1 (PD-1) polymorphisms in Chinese patients with esophageal cancer*, 47 Clinical Biochemistry 612-617 (Online Jan. 2, 2014).
Pardoll, *The blockade of immune checkpoints in cancer immunotherapy*, 12(4) Nat Rev Cancer 252-264 (May 4, 2016).
Shen et al., *Programmed Cell Death Ligand 1 Expression in Osteosarcoma*, 2(7) Cancer Immunol Res. 690-698 (Online Apr. 21, 2014).
Sliwkowski et al., *Antibody Therapeutics in Cancer*, 341 Science 1192-1198 (Sep. 13, 2013).
Topalian et al., *Safety, Activity, and Immune Correlates of Anti-PD-1 Antibody in Cancer*, 366(26) N. Engl. J. Med. 2443-2454 (Jun. 28, 2012).
Zitvogel, *Targeting PD-1/PD-L1 interactions for cancer immunotherapy*, 1(8) OncoImmunology 1223-1225 (Nov. 2012).
OPDIVO® Prescribing Information, Reference ID:4421379, Initial U.S. Approval 2014, Revised Mar. 2019.
Opdivo Approval History https://www.drugs.com/history/opdivo.html (Jul. 26, 2019).
*Study of Pembrolizumab (MK-3475) in Previously-Treated Participants With Advanced Carcinoma of the Esophagus or Esophagogastric Junction (MK-3475-180/KEYNOTE-180)*(First Posted Sep. 24, 2015) (https://www.clinicaltrials.gov/ct2/show/NCT02559687 (Jul. 26, 2019).
*Pembrolizumab With Locally Delivered Radiation Therapy for the Treatment of Metastatic Esophageal Cancers* (First Posted Dec. 30, 2015) (https://www.clinicaltriais.gov/ct2/show/NCT02642809) (Jul. 26, 2019).
*Study of Pembrolizumab (MK-3475) in Platinum Pre-treated Recurrent/ Metastatic Nasopharyngeal Cancer (MK-3475-122/KEYNOTE-122)* (First Posted Nov. 23, 2015) (https://clinicaltrials.gov/ct2/show/NCT02611960) (Jul. 26, 2019).
*Nivolumab Alone or in Combination With Ipilimumab in Treating Patients With Advanced Uterine Leiomyosarcoma* (First Posted Apr. 28, 2015) (https://clinicaltrials.gov/ct2/show/NCT02428192) (Jul. 26, 2019).
*Nivolumab in Treating Patients With Persistent, Recurrent, or Metastatic Cervical Cancer* (First Posted Oct. 6, 2014) (https://clinicaltrials.gov/ct2/show/NCT02257528) (Jul. 26, 2019).
*Nivolumab and Ipilimumab in Treating Patients With HIV Associated Relapsed or Refractory Classical Hodgkin Lymphoma or Solid Tumors That are Metastatic or Cannot Be Removed by Surgery* (First Posted Apr. 6, 2015) https://www.clinicaltrials.gov/ct2/show/NCT02408861) (Jul. 26, 2019).

(56) References Cited

OTHER PUBLICATIONS

*Study of Pembrolizumab (MK-3475) in Participants With Advanced Solid Tumors (MK-3475-158/KEYNOTE-158)* (First Posted Dec. 11, 2015) (https://clinicaltrials.gov/ct2/show/NCT02628067) (Jul. 26, 2019).

*Phase 1/11 Study of PDR001 in Patients With Advanced Malignancies* (First Posted Mar. 31, 2015) (https://clinicaltrials.gov/ct2/show/NCTO2404441) (Jul. 26, 2019).

*Pembrolizumab in Treating Younger Patients With Recurrent Progressive, or Refractory High-Grade Gliomas, Diffuse Intrinsic Pontine Gliomas, Hypermutated Brain Tumors, Ependymoma or Medulloblastoma* (First Posted Feb. 10, 2015) (https://www.clinicaltrials.gov/ct2/show/NCT02359565) (Jul. 26, 2019).

Atkins et al., *Phase 2, multicenter, safety and efficacy study of pidilizumab in patients with metastatic melanoma*, 32(15 Supplemental) Oncology (May 20, 2014).

Garon et al., *Safety and clinical activity of MK-3475 in previously treated patients (pts) with non-small cell lung cancer (NSCLC)*, 30(15 Supplemental) Journal of Clinical Oncology (May 20, 2012).

Kaufman et al., *Poxvirus-based vaccine therapy for patients with advance pancreatic cancer*, 5(60) Journal of Translational Medicine 1-10 (2007).

Kefford et al., *Clinical efficacy and correlation with tumor PD-L1 expression in patients (pts) with melanoma*, 30(15 Supplemental) Journal of Clinical Oncology (May 20, 2014).

Lu et al., *Combined PD-1 blockade and GITR triggering induce a potent antitumor immunity in murine cancer models and synergizes with chemotherapeutic drugs*, 12(36) Journal of Translational Medicine 1-11 (2014).

Nomi et al., *Clinical Significance and Therapeutic Potential of the Programmed Death-1 Ligand/Programmed Death-1 Pathway in Human Pancreatic Cancer*, 13(7) Clin. Cancer. Res. (Apr. 1, 2007).

Shchelkunov et al., *Vaccinia Virus Molecular Biology*, Orthopoxviruses Pathogenic for Humans 37-44 (2005).

Patnaik et al., *Phase I study of MK-3475 (anti-PD-1 monoclonal antibody) in patients with advanced solid tumors*, 30(15 Supplemental) Journal of Clinical Oncology (May 20, 2012).

Part A1: Information Required Under Article 11 (Schedule 2) of the 2002 Regulations, BN Immunotherapeutics, Inc. (Sep. 13, 2012).

Rizvi et al., *Safety and clinical activity of MK-3475 as initial therapy in patients with advanced non-small cell lunch cancer (NSCLC)*, 30(15 Supplemental) Journal of Clinical Oncology (May 20, 2012).

Seiwert et al., *A phase Ib study of MK-3475 in patients with human papillomavirus (HPV)-associated and non-HPV-associated head and neck (H/N) cancer*, 30(15 Supplemental) Journal of Clinical Oncology (May 20, 2012).

Verbrugge et al., *Radiotherapy Increases the Permissiveness of Established Mammary Tumors to Rejection by Immunomodulatory Antibodies*, 72(13) Cancer Res 3163-3174 (Jul. 1, 2012).

Westin et al., *Safety and Activity of PD1 Blockade by Pidilizumab in Combination with Rituximab in Patients with Relapsed Follicular Lymphoma: a Single Group, Open-label, Phase 2 Trial*, 15(1) Lancet Oncol. 69-77 (Jan. 2014).

\* cited by examiner

* indicates statistical significance between selected groups at the indicated time points

* indicates statistical significance between selected groups at the indicated time points

COMBINATION OF ONCOLYTIC VIRUS WITH IMMUNE CHECKPOINT MODULATORS

CROSS-REFERENCE TO RELATED APPLICATIONS

This application is a U.S. National Stage Application pursuant to 35 U.S.C. § 371 of International Patent Application PCT/EP2015/066353, filed on Jul. 16, 2015, and published as WO 2016/009017 on Jan. 21, 2016, which claims priority to European Patent Application 14306155.4, filed on Jul. 16, 2014, all of which are incorporated herein by reference in their entireties for all purposes.

FIELD OF THE INVENTION

The present invention generally relates to the field of oncolytic virotherapy and more specifically to compositions and methods to treat, prevent, or inhibit proliferative diseases, especially cancer. Embodiments include an oncolytic virus for use for the treatment of cancer in combination with one or more immune checkpoint modulator(s). Embodiments also include a kit comprising such components and method of treatment using said oncolytic virus with said one or more immune checkpoint modulator(s).

Each year, cancer is diagnosed in more than 12 million subjects worldwide. In industrialized countries, approximately one person out five will die of cancer. Although a vast number of chemotherapeutics exist, they are often ineffective, especially against malignant and metastatic tumors that establish at a very early stage of the disease. Moreover, antitumor immunity is often ineffective due to the fact that tumor cells have evolved mechanisms to escape host defense. One of the major mechanisms of immune suppression is a process known as "T-cell exhaustion", which results from chronic exposure to antigens and is characterized by the upregulation of inhibitory receptors. These inhibitory receptors serve as immune checkpoints in order to prevent uncontrolled immune reactions. Various immune checkpoints acting at different levels of T cell immunity have been described in the literature, including programmed cell death protein 1 (PD-1) and its ligands PD-L1 and PD-L2, CTLA-4 (cytotoxic T-lymphocyte associated protein-4), LAG3 (Lymphocyte-activation gene 3), B and T lymphocyte attenuator, T-cell immunoglobulin, mucin domain-containing protein 3 (TIM-3), and V-domain immunoglobulin suppressor of T cell activation.

Whatever the mechanism of action, these immune checkpoints can inhibit the development of an efficient anti-tumor immune response. There is increasing interest in the possible therapeutic benefits of blocking such immune checkpoints as a means of inhibiting immune system tolerance to tumors and thus rescue exhausted antitumor T cells (Leach et al., 1996, Science 271: 1734-6). A vast number of antagonistic antibodies have been developed during the last decade (e.g. anti Tim3, -PD-L1, -CTLA-4, -PD1, etc) and most importantly, some have been associated with objective clinical responses in cancer patients. Antibodies targeting CTLA-4 are already marketed (e.g. Ipilimumab, Yervoy, Bristol-Myers Squibb, BMS) for metastatic melanoma. BMS reported that from 1800 melanoma patients treated with ipilimumab 22% are still alive 3 years later. Antibody therapies with anti PD-L1 (e.g. MPDL3280A, Roche), anti PD-1 (e.g. Nivolumab, BMS) are also ongoing.

Another therapeutic approach that is emerging in the field of cancer is oncolytic viruses (Hermiston, 2006, Curr. Opin. Mol. Ther. 8: 322-30). Oncolytic viruses are capable of selective replication in dividing cells (e.g. cancer cell) while leaving non dividing cells (e.g. normal cells) unharmed. As the infected dividing cells are destroyed by lysis, they release new infectious virus particles to infect the surrounding dividing cells. Cancer cells are ideal hosts for many viruses because they have the antiviral interferon pathway inactivated or have mutated tumour suppressor genes that enable viral replication to proceed unhindered (Chernajovsky et al., 2006, British Med. J. 332: 170-2). A number of viruses including adenovirus, reovirus, measles, herpes simplex, Newcastle disease virus and vaccinia have now been clinically tested as oncolytic agents.

Some viruses are naturally oncolytic (such as reovirus and the Seneca valley picornavirus) while others are engineered for tumor selectivity by modifying the viral genome. Such modifications include functional deletions in essential viral genes, the use of tumor- or tissue-specific promoters to control the viral gene expression and tropism modification to redirect virus to the cancer cell surface.

The first oncolytic virus to be approved by a regulatory agency was a genetically modified adenovirus named H101 (Shanghai Sunway Biotech) that gained approval in 2005 from China's State Food and Drug Administration (SFDA) for the treatment of head and neck cancer. Another oncolytic adenovirus, named ONYX-015 is in ongoing clinical trials for the treatment of various solid tumors (in phase III for the treatment of recurrent head and neck cancer) (Cohen et al., 2001, Curr. Opin. Investig. Drugs 2: 1770-5). As another example, oncolytic herpes simplex 1 (T-VEC) was genetically engineered to attenuate the virus virulence, increase selectivity for cancer cells and enhance antitumor immune response (through GM-CSF (Granulocyte-macrophage colony-stimulating factor) expression). Clinical efficacy in unresectable melanoma has been demonstrated in Phase II and Phase III clinical trials (Senzer et al, 2009, J. Clin. Oncol. 27: 5763-71).

Vaccinia viruses (VV) possess many of the key attributes necessary for use in oncolytic virotherapy such as natural tropism for tumors, strong lytic ability, short life cycle with rapid cell-to-cell spread, highly efficient gene expression and a large cloning capacity. In addition, they have been delivered to millions of individuals during the smallpox eradication campaign without major safety concerns. In this respect, a TK (Thymidine Kinase) and VGF (for VV growth factor) double deleted VV expressing GM-CSF (named JX-963) showed significant cancer selectivity in tumor bearing mice (Thorne et al., 2007, J Clin Invest. 117: 3350-8). On the same line, JX-594, a TK-deleted VV (Wyeth strain) armed with GM-CSF, has shown promising clinical data, and a randomized Phase III trial in hepatocellular carcinoma is expected to start soon.

Combination therapies have also been described in the literature. WO2010/014784 describes the combination of an anti CTLA4 antibody with chemotherapeutics used for treating cancer such as GLEEVEC, TAXOL and the like. WO2014/047350 envisages a recombinant oncolytic virus with a gene encoding an anti-PD-1 antibody inserted in the viral genome.

Technical Problem

One may expect that cancer will continue to be a serious global health threat for many years due to the high number of causal factors that may act together or separately to initiate or promote the development of a cancer. Moreover, malignant and especially metastatic tumors are often resistant to conventional therapies explaining the significant morbidity of some cancers.

Thus, there is an important need to develop more effective approaches, for improving prevention and treatment of such proliferative diseases, and especially combination approaches.

The combination therapy, wherein an oncolytic virus and one or more immune checkpoint modulator(s) were both administered, provided a synergistic immune response as compared to either approach used alone. Surprisingly, the combined treatment wherein an oncolytic vaccinia virus was administered before administration of an anti-checkpoint antibody such as anti-PD-1 or anti-CTLA-4, improved the anti-tumor response as evidenced in an appropriate model animal, thus potentially providing an effective and powerful therapy against cancer. Accordingly, the embodiments provided herein provide a significant advance in the treatment and prevention of proliferative diseases such as cancer.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

SUMMARY OF THE INVENTION

The present invention concerns a synergistic combination of oncolytic viruses with one or more immune checkpoint modulator(s) for use for the treatment of proliferative diseases such as cancers. The oncolytic virus is preferably selected from the group consisting of reovirus, New Castle Disease virus (NDV), vesicular stomatitis virus (VSV), measles virus, influenza virus, Sinbis virus, adenovirus, poxvirus and herpes virus (HSV) and the like. In one embodiment, the oncolytic virus is a vaccinia virus. In a preferred embodiment, the vaccinia virus is engineered to lack thymidine kinase (TK) activity (e.g. the genome of said VV has an inactivating mutation in J2R gene or a gene deletion to produce a defective TK phenotype). Alternatively or in combination, the vaccinia virus is engineered to lack ribonucleotide reductase (RR) activity (e.g. the genome of said VV has an inactivating mutation in I4L and/or F4L gene or a gene deletion to produce a defective RR phenotype).

In one embodiment, the vaccinia virus further expresses at least one therapeutic gene, in particular a gene encoding a suicide gene product and/or an immunostimulatory protein.

In one embodiment, the one or more immune checkpoint modulator(s) is an antagonist molecule that antagonizes the activity of PD-1, PD-L1 or CTLA4 with a specific preference for an anti PD-1 antibody and/or an anti CTLA4 antibody.

In one embodiment, the oncolytic virus is preferably formulated for intravenous or intratumoral administration and/or the one or more immune checkpoint modulator(s) is preferably formulated for intravenous or intraperitoneal or intratumoral administration.

The present invention further provides a method for the treatment of a proliferative disease including cancer which comprises administering to a mammal in need thereof synergistically effective amounts of an oncolytic virus as described herein and of one or more immune checkpoint modulator(s) as described herein. In one embodiment, the proliferative disease treated by the method of the invention is cancer and especially melanoma, renal cancer, prostate cancer, breast cancer, colorectal cancer, lung cancer and liver cancer. In one embodiment, the method comprises an additional step in which a pharmaceutically acceptable amount of a prodrug is administered to said mammal. The administration of said prodrug takes place preferably at least 3 days after the administration of said oncolytic virus or virus composition.

The present invention further provides a kit including an oncolytic virus as described herein and one or more immune checkpoint modulator(s) preferably in separate containers.

DETAILED DESCRIPTION

The present invention concerns a combination comprising at least an oncolytic virus and one or more immune checkpoint modulator(s) for use for the treatment of proliferative diseases such as cancer.

Definitions

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "one or more" refers to either one or a number above one (e.g. 2, 3, 4, 5, etc).

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. Thus, a polypeptide "comprises" an amino acid sequence when the amino acid sequence might be part of the final amino acid sequence of the polypeptide. Such a polypeptide can have up to several hundred additional amino acids residues. "Consisting essentially of" means excluding other components or steps of any essential significance. Thus, a composition consisting essentially of the recited components would not exclude trace contaminants and pharmaceutically acceptable carriers. A polypeptide "consists essentially of" an amino acid sequence when such an amino acid sequence is present with eventually only a few additional amino acid residues. "Consisting of" means excluding more than trace elements of other components or steps. For example, a polypeptide "consists of" an amino acid sequence when the polypeptide does not contain any amino acids but the recited amino acid sequence.

The terms "polypeptide", "peptide" and "protein" refer to polymers of amino acid residues which comprise at least nine or more amino acids bonded via peptide bonds. The polymer can be linear, branched or cyclic and may comprise naturally occurring and/or amino acid analogs and it may be interrupted by non-amino acids. As a general indication, if the amino acid polymer is more than 50 amino acid residues, it is preferably referred to as a polypeptide or a protein whereas if it is 50 amino acids long or less, it is referred to as a "peptide".

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g. cDNA, genomic DNA, plasmids, vectors, viral genomes, isolated DNA, probes, primers and any mixture thereof) or polyribonucleotides (RNA) (e.g. mRNA, antisense RNA, SiRNA) or mixed polyribopolydeoxyribonucleotides. They encompass single or double-stranded, linear or circular, natural or synthetic, modified or unmodified polynucleotides. Moreover, a polynucleotide may comprise non-naturally occurring nucleotides and may be interrupted by non-nucleotide components.

The term "analog" as used herein refers to a molecule (polypeptide or nucleic acid) exhibiting one or more modification(s) with respect to the native counterpart. Any modification(s) can be envisaged, including substitution, insertion and/or deletion of one or more nucleotide/amino acid residue(s). Preferred are analogs that retain a degree of sequence identity of at least 80%, preferably at least 85%, more preferably at least 90%, and even more preferably at least 98% identity with the sequence of the native counterpart.

In a general manner, the term "identity" refers to an amino acid to amino acid or nucleotide to nucleotide correspondence between two polypeptide or nucleic acid sequences. The percentage of identity between two sequences is a function of the number of identical positions shared by the sequences, taking into account the number of gaps which need to be introduced for optimal alignment and the length of each gap. Various computer programs and mathematical algorithms are available in the art to determine the percentage of identity between amino acid sequences, such as for example the Blast program available at NCBI or ALIGN in Atlas of Protein Sequence and Structure (Dayhoffed, 1981, Suppl., 3: 482-9). Programs for determining identity between nucleotide sequences are also available in specialized data base (e.g. Genbank, the Wisconsin Sequence Analysis Package, BESTFIT, FASTA and GAP programs). For illustrative purposes, "at least 80% identity" means 80%, 81%, 82%, 83%, 84%, 85%, 86%, 87%, 88%, 89%, 90%, 91%, 92%, 93%, 94%, 95%, 96%, 97%, 98%, 99% or 100%.

As used herein, the term "isolated" refers to a protein, polypeptide, peptide, polynucleotide, vector, etc., that is removed from its natural environment (i.e. separated from at least one other component(s) with which it is naturally associated or found in nature). For example, a nucleotide sequence is isolated when it is separated of sequences normally associated with it in nature (e.g. dissociated from a genome) but it can be associated with heterologous sequences.

The term "obtained from", "originating" or "originate" is used to identify the original source of a component (e.g. polypeptide, nucleic acid molecule) but is not meant to limit the method by which the component is made which can be, for example, by chemical synthesis or recombinant means.

As used herein, the term "host cell" should be understood broadly without any limitation concerning particular organization in tissue, organ, or isolated cells. Such cells may be of a unique type of cells or a group of different types of cells such as cultured cell lines, primary cells and dividing cells. In the context of the invention, the term "host cells" include prokaryotic cells, lower eukaryotic cells such as yeast, and other eukaryotic cells such as insect cells, plant and mammalian (e.g. human or non-human) cells as well as cells capable of producing the oncolytic virus and/or the immune checkpoint modulator(s) for use in the invention. This term also includes cells which can be or has been the recipient of the vectors described herein as well as progeny of such cells.

As used herein, the term "oncolytic virus" refers to a virus capable of selectively replicating in dividing cells (e.g. a proliferative cell such as a cancer cell) with the aim of slowing the growth and/or lysing said dividing cell, either in vitro or in vivo, while showing no or minimal replication in non-dividing cells. Typically, an oncolytic virus contains a viral genome packaged into a viral particle (or virion) and is infectious (i.e. capable of infecting and entering into a host cell or subject).

The term "treatment" (and any form of treatment such as "treating", "treat") as used herein encompasses prophylaxis (e.g. preventive measure in a subject at risk of having the pathological condition to be treated) and/or therapy (e.g. in a subject diagnosed as having the pathological condition), eventually in association with conventional therapeutic modalities. The result of the treatment is to slow down, cure, ameliorate or control the progression of the targeted pathological condition. For example, a subject is successfully treated for a cancer if after administration of an oncolytic virus and of one or more immune check point modulator(s) as described herein, the subject shows an observable improvement of its clinical status.

The term "administering" (or any form of administration such as "administered") as used herein refers to the delivery to a subject of a therapeutic agent such as the oncolytic virus and/or the immune checkpoint modulator(s) described herein.

As used herein, the term "proliferative disease" encompasses any disease or condition resulting from uncontrolled cell growth and spread including cancers as well as diseases associated to an increased osteoclast activity (e.g. rheumatoid arthritis, osteoporosis, etc) and cardiovascular diseases (restenosis that results from the proliferation of the smooth muscle cells of the blood vessel wall, etc). The term "cancer" may be used interchangeably with any of the terms "tumor", "malignancy", "neoplasm", etc. These terms are meant to include any type of tissue, organ or cell, any stage of malignancy (e.g. from a prelesion to stage IV)

The term "subject" generally refers to an organism for whom any product and method of the invention is needed or may be beneficial. Typically, the organism is a mammal, particularly a mammal selected from the group consisting of domestic animals, farm animals, sport animals, and primates. Preferably, the subject is a human who has been diagnosed as having or at risk of having a proliferative disease such as a cancer. The terms "subject" and "patients" may be used interchangeably when referring to a human organism and encompasses male and female. The subject to be treated may be a newborn, an infant, a young adult or an adult.

The term "combination" as used herein refers to any arrangement possible of various components (e.g. oncolytic virus and immune checkpoint modulator(s)). Such an arrangement includes mixture of at least one oncolytic virus with one or more immune check point modulator(s) in the form of polypeptides (e.g. recombinant antibody or mixture of recombinant antibodies) or nucleic acid molecule(s) (e.g. carried by one or more vector engineered for expressing such one or more immune checkpoint modulator(s)) as well as mixture of polypeptide(s) and nucleic acid molecule(s) (e.g. a recombinant antibody and an expressing vector). The present invention encompasses combinations comprising equal molar concentrations of each immune checkpoint modulator when more than one is used as well as combinations with very different concentrations. It is appreciated that optimal concentration of each component of the combination can be determined by the artisan skilled in the art. Preferably the combination is synergistic providing higher efficacy than each entity alone.

The term "immune checkpoint modulator" refers to a molecule capable of modulating the function of an immune checkpoint protein in a positive or negative way (in particular the interaction between an antigen presenting cell (APC) such as a cancer cell and an immune T effector cell). The term "immune checkpoint" refers to a protein directly or indirectly involved in an immune pathway that under normal physiological conditions is crucial for preventing uncontrolled immune reactions and thus for the maintenance of self-tolerance and/or tissue protection. The one or more immune checkpoint modulator(s) in use herein may independently act at any step of the T cell-mediated immunity including clonal selection of antigen-specific cells, T cell activation, proliferation, trafficking to sites of antigen and inflammation, execution of direct effector function and signaling through cytokines and membrane ligands. Each of these steps is regulated by counterbalancing stimulatory and inhibitory signals that in fine tune the response. In the context of the present invention, the term encompasses immune checkpoint modulator(s) capable of down-regulating at least partially the function of an inhibitory immune checkpoint (antagonist) and/or immune checkpoint modulator(s) capable of up-regulating at least partially the function of a stimulatory immune checkpoint (agonist).

Oncolytic Virus

The oncolytic virus for use in the present invention can be obtained from any member of virus identified at present time provided that it is oncolytic by its propensity to selectivity replicate and kill dividing cells as compared to non-dividing cells. It may be a native virus that is naturally oncolytic or may be engineered by modifying one or more viral genes so as to increase tumor selectivity and/or preferential replication in dividing cells, such as those involved in DNA replication, nucleic acid metabolism, host tropism, surface attachment, virulence, lysis and spread (see for example Kirn et al., 2001, Nat. Med. 7: 781; Wong et al., 2010, Viruses 2: 78-106). One may also envisage placing one or more viral gene(s) under the control of event or tissue-specific regulatory elements (e.g. promoter).

Exemplary oncolytic viruses include without limitation reovirus, Seneca Valley virus (SVV), vesicular stomatitis virus (VSV), Newcastle disease virus (NDV), herpes simplex virus (HSV), morbillivirus virus, retrovirus, influenza virus, Sin bis virus, poxvirus, adenovirus, or the like.

In one embodiment, the oncolytic virus for use in the present invention is obtained from a reovirus. A representative example includes Reolysin (under development by Oncolytics Biotech; NCT01166542).

In one embodiment, the oncolytic virus for use in the present invention is obtained from a Seneca Valley virus. A representative example includes NTX-010 (Rudin et al., 2011, Clin. Cancer. Res. 17(4): 888-95).

In one embodiment, the oncolytic virus for use in the present invention is obtained from a vesicular stomatitis virus (VSV). Representative examples for use in the invention are described in the literature (e.g. Stojdl et al., 2000, Nat. Med. 6(7): 821-5; Stojdl et al., 2003, Cancer Cell 4(4): 263-75).

In one embodiment, the oncolytic virus for use in the present invention is obtained from a Newcastle disease virus. Representative examples for use in the invention include without limitation the 73-T PV701 and HDV-HUJ strains as well as those described in the literature (e.g. Phuangsab et al., 2001, Cancer Lett. 172(1): 27-36; Lorence et al., 2007, Curr. Cancer Drug Targets 7(2): 157-67; Freeman et al., 2006, Mol. Ther. 13(1): 221-8).

In one embodiment, the oncolytic virus for use in the present invention is obtained from a herpes simplex virus (HSV). The Herpesviridae are a large family of DNA viruses that all share a common structure and are composed of relatively large double-stranded, linear DNA genomes encoding 100-200 genes encapsided within an icosahedral capsid which is enveloped in a lipid bilayer membrane. Although the oncolytic herpes virus can be derived from different types of HSV, particularly preferred are HSV1 and HSV2. The herpes virus may be genetically modified so as to restrict viral replication in tumors or reduce its cytotoxicity in non-dividing cells. For example, any viral gene involved in nucleic acid metabolism may be inactivated, such as thymidine kinase (Martuza et al., 1991, Science 252: 854-6), ribonucleotide reductase (RR) (Boviatsis et al., 1994, Gene Ther. 1: 323-31; Mineta et al., 1994, Cancer Res. 54: 3363-66), or uracil-N-glycosylase (Pyles et al., 1994, J. Virol. 68: 4963-72). Another aspect involves viral mutants with defects in the function of genes encoding virulence factors such as the ICP34.5 gene (Chambers et al., 1995, Proc. Natl. Acad. Sci. USA 92: 1411-5). Representative examples of oncolytic herpes virus include NV1020 (e.g. Geevarghese et al., 2010, Hum. Gene Ther. 21(9): 1119-28) and T-VEC (Andtbacka et al., 2013, J. Clin. Oncol. 31, abstract number LBA9008).

In one embodiment, the oncolytic virus for use in the present invention is obtained from a morbillivirus which can be obtained from the paramyxoviridae family, with a specific preference for measles virus. Representative examples of suitable oncolytic measles viruses include without limitation MV-Edm (McDonald et al., 2006; Breast Cancer Treat. 99(2): 177-84) and HMWMAA (Kaufmann et al., 2013, J. Invest. Dermatol. 133(4): 1034-42)

In one embodiment, the oncolytic virus for use in the present invention is obtained from an adenovirus. Methods are available in the art to engineer oncolytic adenoviruses. An advantageous strategy includes the replacement of viral promoters with tumor-selective promoters or modifications of the E1 adenoviral gene product(s) to inactivate its/their binding function with p53 or retinoblastoma (Rb) protein that are altered in tumor cells. In the natural context, the adenovirus E1B55 kDa gene cooperates with another adenoviral product to inactivate p53 (p53 is frequently dysregulated in cancer cells), thus preventing apoptosis. Representative examples of oncolytic adenovirus include ONYX-015 (e.g. Khuri et al., 2000, Nat. Med 6(8): 879-85) and H101 also named Oncorine (Xia et al., 2004, Ai Zheng 23(12): 1666-70).

In one embodiment, the oncolytic virus for use in the present invention is a poxvirus. As used herein the term "poxvirus" refers to a virus belonging to the Poxviridae family, with a specific preference for a poxvirus belonging to the Chordopoxviridae subfamily and more preferably to the Orthopoxvirus genus. Sequences of the genome of various poxviruses, for example, the vaccinia virus, cowpox virus, Canarypox virus, Ectromelia virus, Myxoma virus genomes are available in the art and specialized databases such as Genbank (accession number NC_006998, NC_003663, NC_005309, NC_004105, NC_001132 respectively).

Desirably, the oncolytic poxvirus is an oncolytic vaccinia virus. Vaccinia viruses are members of the poxvirus family characterized by a 200 kb double-stranded DNA genome that encodes numerous viral enzymes and factors that enable the virus to replicate independently from the host cell machinery. The majority of vaccinia virus particles is intracellular (IMV for intracellular mature virion) with a single lipid envelop and remains in the cytosol of infected cells until lysis. The other infectious form is a double enveloped particle (EEV for extracellular enveloped virion) that buds out from the infected cell without lysing it.

Although it can derive from any vaccinia virus strain, Elstree, Wyeth, Copenhagen and Western Reserve strains are particularly preferred. The gene nomenclature used herein is that of Copenhagen vaccinia strain. It is also used herein for the homologous genes of other poxviridae unless otherwise indicated. However, gene nomenclature may be different according to the pox strain but correspondence between Copenhagen and other vaccinia strains are generally available in the literature.

Preferably, the oncolytic vaccinia virus for use in the present invention is modified by altering one or more viral gene(s). Said modification(s) preferably lead(s) to the synthesis (or lack of synthesis) of a defective protein unable to ensure the activity of the protein produced under normal conditions by the unmodified gene. Modifications encompass deletion, mutation and/or substitution of one or more nucleotide(s) (contiguous or not) within the viral gene or its regulatory elements. Modification(s) can be made in a number of ways known to those skilled in the art using conventional recombinant techniques. Exemplary modifications are disclosed in the literature with a specific preference for those altering viral genes involved in DNA metabolism, host virulence and IFN pathway (see e.g. Guse et al., 2011, Expert Opinion Biol. Ther. 11(5):595-608).

More preferably, the oncolytic poxvirus for use in the present invention is modified by altering the thymidine kinase-encoding gene (locus J2R). The TK enzyme is involved in the synthesis of deoxyribonucleotides. TK is needed for viral replication in normal cells as these cells have generally low concentration of nucleotides whereas it is dispensable in dividing cells which contain high nucleotide concentration.

Alternatively or in combination, the oncolytic poxvirus for use in the present invention is modified by altering at least one gene or both genes encoding Ribonucleotide reductase (RR). In the natural context, this enzyme catalyzes the reduction of ribonucleotides to deoxyribonucleotides that represents a crucial step in DNA biosynthesis. The viral enzyme is similar in subunit structure to the mammalian enzyme, being composed of two heterologous subunits, designed R1 and R2 encoded respectively by the 14L and F4L locus. Sequences for the 14L and F4L genes and their locations in the genome of various poxvirus are available in public databases, for example via accession number DQ437594, DQ437593, DQ377804, AH015635, AY313847, AY313848, NC_003391, NC_003389, NC_003310, M-35027, AY243312, DQ011157, DQ011156, DQ011155, DQ011154, DQ011153, Y16780, X71982, AF438165, U60315, AF410153, AF380138, U86916, L22579, NC_006998, DQ121394 and NC_008291. In the context of the invention, either the 14L gene (encoding the R1 large subunit) or the F4L gene (encoding the R2 small subunit) or both may be inactivated.

Alternatively or in combination, other strategies may also be pursued to further increase the virus tumor-specificity. A representative example of suitable modifications includes disruption of the VGF-encoding gene from the viral genome. VGF (for VV growth factor) is a secreted protein which is expressed early after cell infection and its function seems important for virus spread in normal cells. Another example is the disruption of the A56R gene coding for hemagglutinin, eventually in combination with TK deletion (Zhang et al., 2007, Cancer Res. 67: 10038-46). Disruption of interferon modulating gene(s) may also be advantageous (e.g. the B8R or B18R gene) or the caspase-1 inhibitor B13R gene.

In a preferred embodiment, the oncolytic virus for use in this invention is a vaccinia virus defective for TK resulting from inactivating mutations in the J2R gene. In another preferred embodiment, the oncolytic virus for use in this invention is a vaccinia virus defective for both TK and RR activities resulting from inactivating mutations in both the J2R gene and the 14L and/or F4L gene(s) carried by the viral genome (e.g. as described in WO2009/065546 and Foloppe et al., 2008, Gene Ther., 15: 1361-71).

Therapeutic Genes

In one embodiment, the oncolytic virus for use in this invention further expresses at least one therapeutic gene inserted in the viral genome. A "therapeutic gene" encodes a product capable of providing a biological activity when administered appropriately to a subject, which is expected to cause a beneficial effect on the course or a symptom of the pathological condition to be treated by either potentiating anti-tumor efficacy or reinforcing the oncolytic nature of the virus. In the context of the invention, the therapeutic gene can be of human origin or not (e.g. of bacterial, yeast or viral origin). Preferably, the therapeutic gene is not a gene or nucleic acid sequence encoding an immune checkpoint modulator as described herein.

A vast number of therapeutic genes may be envisaged in the context of the invention such as those encoding polypeptides that can compensate for defective or deficient proteins in the subject, or those that act through toxic effects to limit or remove harmful cells from the body or those that encode immunity conferring polypeptides. They may be native genes or genes obtained from the latter by mutation, deletion, substitution and/or addition of one or more nucleotides.

Advantageously, the oncolytic virus in use in the present invention carries a therapeutic gene selected from the group consisting of genes encoding suicide gene products and immunostimulatory proteins.

Suicide Gene

The term "suicide gene" refers to a gene coding for a protein able to convert a precursor of a drug into a cytoxic compound. Suicide genes comprise but are not limited to genes coding protein having a cytosine deaminase activity, a thymidine kinase activity, an uracil phosphoribosyl transferase activity, a purine nucleoside phosphorylase activity and a thymidylate kinase activity. Examples of suicide genes and corresponding precursors of a drug comprising one nucleobase moiety are disclosed in the following table

TABLE 1

| Suicide gene | prodrug |
| --- | --- |
| Thymidine Kinase | Ganciclovir; Ganciclovir elaidic acid ester; penciclovir; Acyclovir; Valacyclovir; (E)-5-(2-bromovinyl)-2'-deoxyuridine; zidovudine; 2'-Exo-methanocarbathymidine |

TABLE 1-continued

| Suicide gene | prodrug |
| --- | --- |
| Cytosine deaminase | 5-Fluorocytosine |
| Purine nucleoside phosphorylase | 6-Methylpurine deoxyriboside; Fludarabine |
| uracil phosphoribosyl transferase | 5-Fluorocytosine; 5-Fluorouracil |
| thymidylate kinase. | Azidothymidine |

Desirably, the suicide gene encodes a protein having at least cytosine deaminase (CDase) activity. In the prokaryotes and lower eukaryotes (it is not present in mammals), CDase is involved in the pyrimidine metabolic pathway by which exogenous cytosine is transformed into uracil by means of a hydrolytic deamination. CDase also deaminates an analogue of cytosine, i.e. 5-fluorocytosine (5-FC), thereby forming 5-fluorouracil (5-FU), a compound which is highly cytotoxic when it is converted into 5-fluoro-UMP (5-FUMP). CDase encoding nucleic acid molecule can be obtained from any prokaryotes and lower eukaryotes such as *Saccharomyces cerevisiae* (FCY1 gene), *Candida Albicans* (FCA1 gene) and *Escherichia coli* (codA gene). The gene sequences and encoded CDase proteins have been published and are available in specialized data banks (SWISSPROT EMBL, Genbank, Medline and the like). Functional analogues of these genes may also be used. Such analogues preferably have a nucleic acid sequence having a degree of identity of at least 70%, advantageously of at least 80%, preferably of at least 90%, and most preferably of at least 95% with the nucleic acid sequence of the native gene.

Alternatively or in combination, the oncolytic virus in use in the invention carries in its viral genome a suicide gene encoding a polypeptide having uracil phosphoribosyl transferase (UPRTase) activity. In prokaryotes and lower eukaryotes, uracil is transformed into UMP by the action of UPRTase. This enzyme converts 5-FU into 5-FUMP. By way of illustration, the nucleic acid sequences encoding the UPRTases from *E. coli* (Andersen et al., 1992, European J. Biochem. 204: 51-56), from *Lactococcus lactis* (Martinussen et al., 1994, J. Bacteriol. 176: 6457-63), from *Mycobacterium bovis* (Kim et al., 1997, Biochem. Mol. Biol. Internat. 41: 1117-24) and from *Bacillus subtilis* (Martinussen et al., 1995, J. Bacteriol. 177: 271-4) may be used in the context of the invention. However, it is most particularly preferred to use a yeast UPRTase and in particular that encoded by the *S. cerevisiae* (FUR1 gene) whose sequence is disclosed in Kern et al. (1990, Gene 88: 149-57). Functional UPRTase analogues may also be used such as the N-terminally truncated FUR1 mutant described in EP998568 (with a deletion of the 35 first residues up to the second Met residue present at position 36 in the native protein) which exhibits a higher UPRTase activity than that of the native enzyme.

Preferably, the suicide gene inserted in the viral genome of the oncolytic virus for use in the present invention encodes a polypeptide having CDase and UPRTase activities. Such a polypeptide can be engineered by fusion of two enzymatic domains, one having the CDase activity and the second having the UPRTase activity. Exemplary polypeptides include without limitation fusion polypeptides codA:: upp, FCY1::FUR1 and FCY1::FUR1[Delta] 105 (FCU1) and FCU1-8 described in WO96/16183, EP998568 and WO2005/07857. Of particular interest is the FCU1 suicide gene (or FCY1::FUR1[Delta] 105 fusion) encoding a polypeptide comprising the amino acid sequence represented in the sequence identifier SEQ ID NO: 1 of WO2009/065546. The present invention encompasses analogs of such polypeptides providing they retain the CDase, and/or UPRTase activities. It is within the reach of the skilled person to isolate the CDase and/or UPRTase-encoding nucleic acid molecules from the published data, eventually engineer analogs thereof and test the enzymatic activity in an acellular or cellular system according to conventional techniques (see e.g. EP998568).

Immunostimulatory Therapeutic Genes

As used herein, the term "immunostimulatory protein" refers to a protein which has the ability to stimulate the immune system, in a specific or non-specific way. A vast number of proteins are known in the art for their ability to exert an immunostimulatory effect. Examples of suitable immunostimulatory proteins in the context of the invention include without limitation cytokines, with a specific preference for interleukins (e.g. IL-2, IL-6, IL-12, IL-15, IL-24), chemokines (e.g. CXCL10, CXCL9, CXCL11), interferons (e.g. IFNg, IFNalpha), tumor necrosis factor (TNF), colony-stimulating factors (e.g. GM-CSF, C-CSF, M-CSF . . . ), APC (for Antigen Presenting Cell)-exposed proteins (e.g. B7.1, B7.2 and the like), growth factors (Transforming Growth Factor TGF, Fibroblast Growth Factor FGF, Vascular Endothelial Growth Factors VEGF, and the like), major histocompatibility complex (MHC) antigens of class I or II, apoptosis inducers or inhibitors (e.g. Bax, Bcl2, BcIX . . . ), cytostatic agents (p21, p16, Rb . . . ), immunotoxins, antigens (antigenic polypeptides, epitopes, and the like) and markers (beta-galactosidase, luciferase . . . ). Preferably, the imunostimulatory protein is an interleukin or a colony-stimulating factor, with a specific preference for GM-CSF.

Expression of the Therapeutic Genes

The therapeutic gene may be easily obtained by cloning, by PCR or by chemical synthesis according to the conventional techniques. In addition, the therapeutic gene can be optimized for providing high level expression in a particular host cell or subject. It has been indeed observed that, the codon usage patterns of organisms are highly non-random and the use of codons may be markedly different between different hosts. As the therapeutic gene might be from bacterial or lower eukaryote origin (e.g. the suicide gene), it may have an inappropriate codon usage pattern for efficient expression in higher eukaryotic cells (e.g. human). Typically, codon optimization is performed by replacing one or more "native" (e.g. bacterial or yeast) codon corresponding to a codon infrequently used in the host organism of interest by one or more codon encoding the same amino acid which is more frequently used. It is not necessary to replace all native codons corresponding to infrequently used codons since increased expression can be achieved even with partial replacement.

Further to optimization of the codon usage, expression in the host cell or subject can further be improved through additional modifications of the gene sequence. For example, the therapeutic gene sequence can be modified so as to prevent clustering of rare, non-optimal codons being present in concentrated areas and/or to suppress or modify "negative" sequence elements which are expected to negatively influence expression levels. Such negative sequence elements include without limitation the regions having very high (>80%) or very low (<30%) GC content; AT-rich or GC-rich sequence stretches; unstable direct or inverted repeat sequences; R A secondary structures; and/or internal cryptic regulatory elements such as internal TATA-boxes, chi-sites, ribosome entry sites, and/or splicing donor/acceptor sites.

In accordance with the present invention, the therapeutic gene(s) inserted in the genome of the oncolytic virus for use in the invention is operably linked to suitable regulatory elements for its expression in a host cell or subject. As used herein, the term "regulatory elements" or "regulatory sequence" refers to any element that allows, contributes or modulates the expression of the therapeutic gene(s) in a given host cell or subject, including replication, duplication, transcription, splicing, translation, stability and/or transport of the nucleic acid(s) or its derivative (i.e. m RNA). As used herein, "operably linked" means that the elements being linked are arranged so that they function in concert for their intended purposes. For example a promoter is operably linked to a nucleic acid molecule if the promoter effects transcription from the transcription initiation to the terminator of said nucleic acid molecule in a permissive host cell.

It will be appreciated by those skilled in the art that the choice of the regulatory sequences can depend on such factors as the gene itself, the virus into which it is inserted, the host cell or subject, the level of expression desired, etc. The promoter is of special importance. In the context of the invention, it can be constitutive directing expression of the therapeutic gene(s) in many types of host cells or specific to certain host cells (e.g. liver-specific regulatory sequences) or regulated in response to specific events or exogenous factors (e.g. by temperature, nutrient additive, hormone, etc) or according to the phase of a viral cycle (e.g. late or early). One may also use promoters that are repressed during the production step in response to specific events or exogenous factors, in order to optimize virus production and circumvent potential toxicity of the expressed polypeptide(s).

Promoters suitable for constitutive expression in mammalian cells include but are not limited to the cytomegalovirus (CMV) immediate early promoter (U.S. Pat. No. 5,168,062), the RSV promoter, the adenovirus major late promoter, the phosphoglycero kinase (PGK) promoter (Adra et al., 1987, Gene 60: 65-74), the thymidine kinase (TK) promoter of herpes simplex virus (HSV)-1 and the T7 polymerase promoter (WO98/10088). Vaccinia virus promoters are particularly adapted for expression in oncolytic poxviruses. Representative examples include without limitation the vaccinia 7.5K, HSR, 11K7.5 (Erbs et al., 2008, Cancer Gene Ther. 15(1): 18-28), TK, p28, p11 and K1L promoter, as well as synthetic promoters such as those described in Chakrabarti et al. (1997, Biotechniques 23: 1094-7; Hammond et al, 1997, J. Virol Methods 66: 135-8; and Kumar and Boyle, 1990, Virology 179: 151-8) as well as early/late chimeric promoters. Promoters suitable for oncolytic measles viruses include without limitation any promoter directing expression of measles transcription units (Brandler and Tangy, 2008, CIMID 31: 271).

Those skilled in the art will appreciate that the regulatory elements controlling the expression of the therapeutic gene (s) may further comprise additional elements for proper initiation, regulation and/or termination of transcription (e.g. polyA transcription termination sequences), mRNA transport (e.g. nuclear localization signal sequences), processing (e.g. splicing signals), and stability (e.g. introns and non-coding 5' and 3' sequences), translation (e.g. an initiator Met, tripartite leader sequences, IRES ribosome binding sites, signal peptides, etc.).

The therapeutic gene can be inserted at any location of the viral genome, with a specific preference for a non-essential locus For example, TK gene is particularly appropriate for insertion in oncolytic vaccinia virus.

In a preferred embodiment, the oncolytic virus for use in the invention is a vaccinia virus (preferably from the Copenhague strain) defective for both TK and RR activities (e.g. resulting from inactivating mutations in both the viral J2R and 14L genes). More preferably, said vaccinia virus is armed with a suicide gene with a special preference for the FCU1 suicide gene described herein. Even more preferably, the suicide gene (e.g. FCU1) is under the transcriptional control of the p11K7.5 vaccinia promoter. Still more preferably, the FCU1 placed under the control of the vaccinia virus promoter is inserted within TK locus of the virus genome.

In an alternative and also preferred embodiment, the oncolytic virus for use in the invention is a vaccinia virus (preferably from the Wyeth strain) defective for TK activity (resulting from inactivating mutations in the virus J2R gene). More preferably, said vaccinia virus is armed with an immunostimulatory therapeutic gene with a special preference for the human GM-CSF gene described herein. Even more preferably, the therapeutic gene (e.g. GM-CSF) is under the transcriptional control of a synthetic early-late promoter vaccinia promoter and is preferably inserted within TK locus.

Typically, the oncolytic virus for use according to the present invention is produced into a suitable host cell line using conventional techniques including culturing the transfected or infected host cell under suitable conditions so as to allow the production of infectious viral particles and recovering the produced infectious viral particles from the culture of said cell and optionally purifying said recovered infectious viral particles. Suitable host cells for production of the oncolytic virus include without limitation human cell lines such as HeLa (ATCC), 293 cells (Graham et al., 1997, J. Gen. Virol. 36: 59-72), HER96, PER-C6 (Fallaux et al., 1998, Human Gene Ther. 9: 1909-17), avian cells such as those described in WO2005/042728, WO2006/108846, WO2008/129058, WO2010/130756, WO2012/001075, etc), hamster cell lines such as BHK-21 (ATCC CCL-10) as well as primary chicken embryo fibroblasts (CEF) prepared from chicken embryos obtained from fertilized eggs. The oncolytic virus can be at least partially isolated before being used according to the present invention. Various purification steps can be envisaged, including clarification, enzymatic treatment (e.g. benzonase, protease), chromatographic and filtration steps. Appropriate methods are described in the art (e.g. WO2007/147528; WO2008/138533, WO2009/100521, WO2010/130753, WO2013/022764).

Immune Checkpoint Modulator(s)

Immune checkpoints and modulators thereof as well as methods of using such compounds are described in the literature. In accordance with this invention, the one or more immune checkpoint modulator(s) may independently be a polypeptide or a polypeptide-encoding nucleic acid molecule; said polypeptide comprising a domain capable of binding the targeted immune checkpoint and/or inhibiting the binding of a ligand to said targeted immune checkpoint so as to exert an antagonist function (i.e. being capable of antagonizing an immune checkpoint-mediated inhibitory signal) or an agonist function (i.e. being capable of boosting an immune checkpoint-mediated stimulatory signal). Such one or more immune checkpoint modulator(s) can be independently selected from the group consisting of peptides (e.g. peptide ligands), soluble domains of natural receptors, RNAi, antisense molecules, antibodies and protein scaffolds.

In a preferred embodiment, the immune checkpoint modulator is an antibody. In the context of the invention, "antibody" ("Ab") is used in the broadest sense and encompasses naturally occurring and engineered by man as well as full length antibodies or functional fragments or analogs thereof that are capable of binding the target immune checkpoint or epitope (thus retaining the target-binding portion). The antibody in use in the invention can be of any origin, e.g. human, humanized, animal (e.g. rodent or camelid antibody) or chimeric. It may be of any isotype with a specific preference for an IgG1 or IgG4 isotype. In addition, it may be glycosylated or non-glycosylated. The term antibody also includes bispecific or multispecific antibodies so long as they exhibit the binding specificity described herein.

For illustrative purposes, full length antibodies are glycoproteins comprising at least two heavy (H) chains and two light (L) chains inter-connected by disulfide bonds. Each heavy chain is comprised of a heavy chain variable region (VH) and a heavy chain constant region which is made of three CH1, CH2 and CH3 domains (eventually with a hinge between CH1 and CH2). Each light chain is comprised of a light chain variable region (VL) and a light chain constant region which comprises one CL domain. The VH and VL regions comprise hypervariable regions, named complementarity determining regions (CDR), interspersed with more conserved regions named framework regions (FR). Each VH and VL is composed of three CDRs and four FRs in the following order: FR1-CDR1-FR2-CDR2-FR3-CDR3-FR4. The CDR regions of the heavy and light chains are determinant for the binding specificity.

As used herein, an "humanized antibody" refers to a non-human (e.g. murine, camel, rat, etc) antibody whose protein sequence has been modified to increase its similarity to a human antibody (i.e. produced naturally in humans). The process of humanization is well known in the art (see e.g. Presta et al., 1997, Cancer Res. 57(20): 4593-9; U.S. Pat. Nos. 5,225,539; 5,530,101; 6,180,370; WO2012/110360). For example, a monoclonal antibody developed for human use can be humanized by substituting one or more residue of the FR regions to look like human immunoglobulin sequence whereas the vast majority of the residues of the variable regions (especially the CDRs) are not modified and correspond to those of a non-human immunoglobulin. For general guidance, the number of these amino acid substitutions in the FR regions is typically no more than 20 in each variable region VH or VL.

As used herein, a "chimeric antibody" refers to an antibody comprising one or more element(s) of one species and one or more element(s) of another species, for example, a non-human antibody comprising at least a portion of a constant region (Fc) of a human immunoglobulin.

Many forms of antibody can be engineered for use in the combination of the invention. Representative examples include without limitation Fab, Fab', F(ab')2, dAb, Fd, Fv, scFv, di-scFv and diabody, etc. More specifically:

(i) a Fab fragment represented by a monovalent fragment consisting of the VL, VH, CL and CH1 domains;
(ii) a F(ab')2 fragment represented by a bivalent fragment comprising two Fab fragments linked by at least one disulfide bridge at the hinge region;
(iii) a Fd fragment consisting of the VH and CH1 domains;
(iv) a Fv fragment consisting of the VL and VH domains of a single arm of an antibody,
(v) a dAb fragment consisting of a single variable domain fragment (VH or VL domain);
(vi) a single chain Fv (scFv) comprising the two domains of a Fv fragment, VL and VH, that are fused together, eventually with a linker to make a single protein chain (see e.g. Bird et al., 1988, Science 242: 423-6; Huston et al., 1988, Proc. Natl. Acad. Sci. USA 85: 5879-83; U.S. Pat. Nos. 4,946,778; 5,258,498); and
(vii) any other artificial antibody.

Methods for preparing antibodies, fragments and analogs thereof are known in the art (see e.g. Harlow and Lane, 1988, Antibodies—A laboratory manual; Cold Spring Harbor Laboratory, Cold Spring Harbor N.Y.). One may cite for example hybridoma technology (as described in Kohler and Milstein, 1975, Nature 256: 495-7; Cote et al., 1983, Proc. Natl. Acad. Sci. USA 80: 2026-30; Cole et al. in Monoclonal antibodies and Cancer Therapy; Alan Liss pp 77-96), recombinant techniques (e.g. using phage display methods), peptide synthesis and enzymatic cleavage. Antibody fragments can be produced by recombinant technique as described herein. They may also be produced by proteolytic cleavage with enzymes such as papain to produce Fab fragments or pepsin to produce F(ab')2 fragments as described in the literature (see e.g. Wahl et al., 1983, J. Nucl. Med. 24: 316-25). Analogs (or fragment thereof) can be generated by conventional molecular biology methods (PCR, mutagenesis techniques). If needed, such fragments and analogs may be screened for functionality in the same manner as with intact antibodies (e.g. by standard ELISA assay).

In a preferred embodiment, at least one of the one or more immune checkpoint modulator(s) for use in the present invention is a monoclonal antibody, with a specific preference for a human (in which both the framework regions are derived from human germline immunoglobin sequences) or a humanized antibody according to well-known humanization process.

Desirably, the one or more immune checkpoint modulator(s) in use in the present invention antagonizes at least partially (e.g. more than 50%) the activity of inhibitory immune checkpoint(s), in particular those mediated by any of the following PD-1, PD-L1, PD-L2, LAG3, Tim3, KIR, BTLA and CTLA4, with a specific preference for a monoclonal antibody that specifically binds to any of such target proteins. The term "specifically binds to" refers to the capacity to a binding specificity and affinity for a particular target or epitope even in the presence of a heterogeneous population of other proteins and biologics. Thus, under designated assay conditions, the antibody in use in the invention binds preferentially to its target and does not bind in a significant amount to other components present in a test sample or subject. Preferably, such an antibody shows high affinity binding to its target with an equilibrium dissociation constant equal or below $1\times10^{-6}$M (e.g. at least $0.5\times10^{-6}$, $1\times10^{-7}$, $1\times10^{-8}$, $1\times10^{-9}$, $1\times10^{-10}$, etc). Alternatively, the one or more immune checkpoint modulator(s) in use in the present invention exerts an agonist function in the sense that it is capable of stimulating or reinforcing stimulatory signals, in particular those mediated by CD28 with a specific preference for any of ICOS, CD137 (or 4-1BB), OX40, CD27, CD40 and GITR immune checkpoints. Standard assays to evaluate the binding ability of the antibodies toward immune checkpoints are known in the art, including for example, ELISAs, Western blots, RIAs and flow cytometry. The binding kinetics (e.g., binding affinity) of the antibodies also can be assessed by standard assays known in the art, such as by Biacore analysis.

In a preferred embodiment, at least one of the one or more checkpoint modulator(s) for use in this invention comprises a human or a humanized antibody capable of antagonizing an immune checkpoint involved in T cell-mediated response. A preferred example of immune checkpoint modulator is represented by a modulator capable of antagonizing at least partially the protein Programmed Death 1 (PD-1), and especially an antibody that specifically binds to human PD-1. PD-1 is part of the immunoglobulin (Ig) gene superfamily and a member of the CD28 family. It is a 55 kDa type 1 transmembrane protein expressed on antigen-experienced cells (e.g. activated B cells, T cells, and myeloid cells) (Agata et al., 1996, Int. Immunol. 8: 765-72; Okazaki et al., 2002, Curr. Opin. Immunol. 14: 391779-82; Bennett et al., 2003, J. Immunol 170: 711-8). In normal context, it acts by limiting the activity of T cells at the time of inflammatory response, thereby protecting normal tissues from destruction (Topalian, 2012, Curr. Opin. Immunol. 24: 207-12). Two ligands have been identified for PD-1, respectively PD-L1 (programmed death ligand 1) and PD-L2 (programmed death ligand 2) (Freeman et al., 2000, J. Exp. Med. 192: 1027-34; Carter et al., 2002, Eur. J. Immunol. 32: 634-43). PD-L1 was identified in 20-50% of human cancers (Dong et al., 2002, Nat. Med. 8: 787-9). The interaction between PD-1 and PD-L1 resulted in a decrease in tumor infiltrating lymphocytes, a decrease in T-cell receptor mediated proliferation, and immune evasion by the cancerous cells (Dong et al., 2003, J. Mol. Med. 81: 281-7; Blank et al., 2005, Cancer Immunol. Immunother. 54: 307-314). The complete nucleotide and amino acid PD-1 sequences can be found under GenBank Accession No U64863 and NP_005009.2. A number of anti PD1 antibodies are available in the art (see e.g. those described in WO2004/004771; WO2004/056875; WO2006/121168; WO2008/156712; WO2009/014708; WO2009/114335; WO2013/043569; and WO2014/047350). Preferred anti PD-1 antibodies in the context of this invention are FDA approved or under advanced clinical development and one may use in particular an anti-PD-1 antibody selected from the group consisting of Nivolumab (also termed BMS-936558 under development by Bristol Myer Squibb), Pembrolizumab (also termed Lanbrolizumab or MK-3475; under development by Merck), and Pidilizumab (also termed CT-011 under development by CureTech).

Another preferred example of immune checkpoint modulator is represented by a modulator capable of antagonizing at least partially the PD-1 ligand termed PD-L1, and especially an antibody that recognizes human PD-L1. A number of anti PD-L1 antibodies are available in the art (see e.g. those described in EP1907000). Preferred anti PD-L1 antibodies are FDA approved or under advanced clinical development (e.g. MPDL3280A under development by Genentech/Roche and BMS-936559 under development by Bristol Myer Squibb).

Still another preferred example of immune checkpoint modulator is represented by a modulator capable of antagonizing at least partially the CTLA-4 protein, and especially an antibody that recognizes human CTLA-4. CTLA4 (for cytotoxic T-lymphocyte-associated antigen 4) also known as CD152 was identified in 1987 (Brunet et al., 1987, Nature 328: 267-70) and is encoded by the CTLA4 gene (Dariavach et al., Eur. J. Immunol. 18: 1901-5). CTLA4 is a member of the immunoglobulin superfamily of receptors. It is expressed on the surface of helper T cells where it primarily regulates the amplitude of the early stages of T cell activation. Recent work has suggested that CTLA-4 may function in vivo by capturing and removing B7-1 and B7-2 from the membranes of antigen-presenting cells, thus making these unavailable for triggering of CD28 (Qureshi et al., Science, 2011, 332: 600-3). The complete CTLA-4 nucleic acid sequence can be found under GenBank Accession No LI 5006. A number of anti CTLA-4 antibodies are available in the art (see e.g. those described in U.S. Pat. No. 8,491,895). Preferred anti CTLA-4 antibodies in the context of this invention are FDA approved or under advanced clinical development. One may cite more particularly ipilimumab marketed by Bristol Myer Squibb as Yervoy (see e.g. U.S. Pat. Nos. 6,984,720; 8,017,114), tremelimumab under development by—Pfizer (see e.g. U.S. Pat. Nos. 7,109,003 and 8,143,379) and single chain anti-CTLA4 antibodies (see e.g. WO97/20574 and WO2007/123737).

Immune checkpoint modulator for antagonizing the LAG3 receptor may also be used in the combination of the present invention (see e.g. U.S. Pat. No. 5,773,578).

Another example of immune checkpoint modulator is represented by an OX40 agonist such as agonist ligand of OX40 (OX40L) (see e.g. U.S. Pat. Nos. 5,457,035, 7,622, 444; WO03/082919) or an antibody directed to the OX40 receptor (see e.g. U.S. Pat. No. 7,291,331 and WO03/106498).

Other examples of immune checkpoint modulators are represented by anti-KIR or anti-CD96 antibody targeting the inhibitory receptors harboured by CD8+ T cells and NK cells.

The present invention encompasses a combination comprising more than one immune checkpoint modulator. A preferred example includes without limitation using an anti-CTLA-4 antibody and an anti-PD-1 antibody in combination with an oncolytic virus as described herein.

Production of Immune Checkpoint Modulator

The one or more immune checkpoint modulator(s) for use in this invention can be produced by recombinant means using suitable expression vectors and host cells.

Nucleic acid molecules encoding the relevant portion(s) of the desired immune checkpoint modulator can be obtained using standard molecular biology techniques (e.g. PCR amplification, cDNA cloning, chemical synthesis) using sequence data accessible in the art and the information provided herein. For example, cDNAs encoding the light and heavy chains of the antibody or their CDRs can be isolated from the producing hybridoma, immunoglobulin gene libraries or any available source.

In one embodiment, the nucleic acid molecule(s) encoding the immune checkpoint modulator(s) can be cloned in a suitable vector and expressed in a host cell to produce said immune checkpoint modulator by recombinant means. Insertion into the expression vector can be performed by routine molecular biology, e.g. as described in Sambrook et al. (2001, Molecular Cloning-A Laboratory Manual, Cold Spring Harbor Laboratory). Insertion into an adenoviral vector or a poxviral vector can be performed through homologous recombination as described respectively in Chartier et al. (1996, J. Virol. 70: 4805-10) and Paul et al. (2002, Cancer gene Ther. 9: 470-7). As described herein in connection with the therapeutic gene, the nucleic acid molecule(s) encoding the immune checkpoint modulator(s) may also be optimized for increasing expression levels.

A variety of host-vector systems may be used or constructed to express the one or more immune checkpoint modulator(s) for use in the present invention, including prokaryotic organisms such as bacteria (e.g. *E. coli* or *Bacillus subtilis*); yeast (e.g. *Saccharomyces cerevisiae, Saccharomyces pombe, Pichia pastoris*); insect cell systems (e.g. Sf 9 cells and baculovirus); plant cell systems (e.g. cauliflower mosaic virus CaMV; tobacco mosaic virus TMV) and mammalian cell systems (e.g. cultured cells). Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the artisan to apply them.

Suitable vectors for use in prokaryotic systems include without limitation pBR322 (Gibco BRL), pUC (Gibco BRL), pbluescript (Stratagene), p Poly (Lathe et al., 1987, Gene 57: 193-201), pTrc (Amann et al., 1988, Gene 69: 301-15); pET lid (Studier et al., 1990, Gene Expression Technology: Methods in Enzymology 185: 60-89); pIN (Inouye et al., 1985, Nucleic Acids Res. 13: 3101-9; Van Heeke et al., 1989, J. Biol. Chem. 264: 5503-9); and pGEX vectors where the nucleic acid molecule can be expressed in fusion with glutathione S-transferase (GST) (Amersham Biosciences Product).

Suitable vectors for expression in yeast (e.g. *S. cerevisiae*) include, but are not limited to pYepSecl (Baldari et al., 1987, EMBO J. 6: 229-34), pMFa (Kujan et al., 1982, Cell 30: 933-43), pJRY88 (Schultz et al., 1987, Gene 54: 113-23), pYES2 (Invitrogen Corporation) and pTEF-MF (Dualsystems Biotech Product).

Suitable plasmid vectors for expression in mammalian host cells include, without limitation, pREP4, pCEP4 (Invitrogene), pCI (Promega), pCDM8 (Seed, 1987, Nature 329: 840) and pMT2PC (Kaufman et al., 1987, EMBO J. 6: 187-95), pVAX and pgWiz (Gene Therapy System Inc; Himoudi et al., 2002, J. Virol. 76: 12735-46).

Viral-based expression systems can also be utilized in the context of the invention derived from a variety of different viruses (e.g. baculovirus, retrovirus, adenovirus, AAV, poxvirus, measles virus, and the like). As used herein, the term "viral vector" encompasses vector DNA as well as viral particles generated thereof. Viral vectors are preferably replication-defective or replication-impaired.

Moreover, the expression vector used in the context of the present invention may also comprise one or more additional element(s) enabling maintenance, propagation or expression of the nucleic acid molecule encoding the immune checkpoint modulator in the host cell. Such additional elements include without limitation marker gene(s) in order to facilitate identification and isolation of the recombinant host cells (e.g. by complementation of a cell auxotrophy or by antibiotic resistance), stabilising elements (e.g. cer sequence as described in Summers and Sherrat, 1984, Cell 36: 1097-103 and DAP system as described in U.S. Pat. No. 5,198,343), and integrative elements (e.g. LTR viral sequences and transposons).

Suitable marker genes for expression in prokaryotic host cells include tetracycline and ampicillin-resistance genes. Also, resistance genes can be used for expression in mammalian host cells such as dihydrofolate reductase (dhfr) which confers resistance to methotrexate (Wigler et al., 1980, Proc. Natl. Acad. Sci. USA 77: 3567; O'Hare et al., 1981, Proc. Natl. Acad. Sci. USA 78: 1527); gpt which confers resistance to mycophenolic acid (Mulligan and Berg, 1981, Proc. Natl. Acad. Sci. USA 78: 2072); neo which confers resistance to the aminoglycoside G-418 (Colberre-Garapin et al., 1981, J. Mol. Biol. 150: 1); zeo which confers resistance to zeomycin, kana which confers resistance to kanamycin and hygro, which confers resistance to hygromycin (Santerre et al., 1984, Gene 30: 147). URA3 and LEU2 genes can be used for expression in yeast systems, which provide for complementation of ura3 or leu2 yeast mutants.

The expression vector can, where appropriate, be combined with one or more substances which improve the transfectional efficiency and/or stability of the vector. These substances are widely documented in the literature. Representative examples of transfection reagents able to facilitate introduction of the vector in the host cell, include without limitation polycationic polymers (e.g. chitosan, polymethacrylate, PEI, etc), cationic lipids (e.g.DC-Chol/DOPE, transfectam lipofectin now available from Promega) and liposomes.

Recombinant DNA technologies can also be used to improve expression of the nucleic acid molecule in the host cell, e.g. by using high-copy number vectors, substituting or modifying one or more transcriptional regulatory sequences (e.g. promoter, enhancer and the like), optimizing the codon usage to the host cell, and suppressing negative sequences that may destabilize the transcript.

Preferably, the nucleic acid molecule encoding the immune checkpoint modulator is in a form suitable for its expression in a host cell, which means that the nucleic acid molecule is placed under the control of one or more regulatory sequences, appropriate to the vector, the host cell and/or the level of expression desired as described in connection with the therapeutic gene.

Promoters suitable for expression in *E. Coli* host cell include, but are not limited to, the bacteriophage lambda pL promoter, the lac, TRP and IPTG-inducible pTAC promoters. Promoters suitable for expression in yeast include the TEF (Mumberg et al., 1995, Gene 156: 119-22), PGK (Hitzeman et al., 1983, Science 219: 620-5), MF alpha (Inokuchi et al., 1987, Mol. Cell. Biol. 7: 3185-93), CYC-1 (Guarente et al, 1981, Proc. Natl. Acad. Sci. USA 78: 2199), GAL-1, GAL4, GAL10, PHO5, glyceraldehyde-3-phosphate dehydrogenase (GAP or GAPDH), and alcohol dehydrogenase (ADH) (Denis et al., 1983, J. Biol. Chem. 25: 1165) promoters. Inducible eukaryotic promoters regulated by exogenously supplied compounds can also be used, including without limitation, the zinc-inducible metallothionein (MT) promoter (Mc Ivor et al., 1987, Mol. Cell Biol. 7: 838-48), the dexamethasone (Dex)-inducible mouse mammary tumor virus (MMTV) promoter, the ecdysone insect promoter (No et al., 1996, Proc. Natl. Acad. Sci. USA 93: 3346-51), the tetracycline-repressible promoter (Gossen et al., 1992, Proc. Natl. Acad. Sci. USA 89: 5547-51), the tetracycline-inducible promoter (Kim et al., 1995, J. Virol. 69: 2565-73), the RU486-inducible promoter (Wang et al., 1997, Nat. Biotech. 15: 239-43) and the rapamycin-inducible promoter (Magari et al., 1997, J. Clin. Invest. 100: 2865-72). Finally, the promoters described for expression of the therapeutic gene are also suitable especially for expression of the one or more immune checkpoint modulator, especially in mammalian cells.

In accordance with the present invention, the immune checkpoint modulator can be modified. Various modifications can be contemplated such as those modifying the amino acid sequence as well as those aimed at increasing its biological half-life, its affinity or its stability.

For example, a signal peptide may be included for facilitating secretion of the immune checkpoint modulator in the cell culture. The signal peptide is typically inserted at the N-terminus of the protein immediately after the Met initiator. The choice of signal peptides is wide and is accessible to persons skilled in the art.

As an additional example, a tag peptide (typically a short peptide sequence able to be recognized by available antisera or compounds) may be also be added for facilitating purification of the recombinant immune checkpoint modulator. A vast variety of tag peptides can be used in the context of the invention including, without limitation, PK tag, FLAG octapeptide, MYC tag, HIS tag (usually a stretch of 4 to 10 histidine residues) and e-tag (U.S. Pat. No. 6,686,152). The tag peptide(s) may be independently positioned at the N-terminus of the protein or alternatively at its C-terminus or alternatively internally or at any of these positions when several tags are employed. Tag peptides can be detected by immunodetection assays using anti-tag antibodies.

As another example, the glycosylation of the immune checkpoint modulator can be altered so as to increase its affinity for its target. Such modifications can be accomplished, for example, by mutating one or more residues within the site(s) of glycosylation. Alternatively, the type of glycosylation can be modified, for example, by expression in a host cell with altered glycosylation machinery. For illustrative purposes, non-glycosylated protein may be expressed in E. coli whereas modulator lacking fucose on their carbohydrates may be produced in other cells such as those described in US 2004-0110704 (lacking the alpha (1,6) fucosyltransferase activity). Such altered glycosylation patterns have been described to increase the ADCC ability of antibodies.

Another modification is pegylation, for example, to increase the biological half-life of the antibody. Methods for pegylating proteins are known in the art (see e.g. EP154316; EP401384; WO98/15293, WO01/23001, etc).

Another approach that may be pursued in the context of the present invention is coupling of the immune checkpoint modulator to an external agent such as a radiosensitizer agent, a cytotoxic agent and/or a labelling agent. The coupling can be covalent or not. As used herein, the term "radiosensitizer" refers to a molecule that makes cells more sensitive to radiation therapy. Radiosensitizer includes, but are not limited to, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuhdine (IUdR), bromodeoxycytidine, fluorodeoxyuridine (FUdR), hydroxyurea and cisplatin.

As used herein, the term "cytoxic agent" refers to a compound that is directly toxic to cells, preventing their reproduction or growth such as toxins (e. g. an enzymatically active toxin of bacterial, fungal, plant or animal origin, or fragments thereof). As used herein, "a labeling agent" refers to a detectable compound. The labeling agent may be detectable by itself (e. g., radioactive isotope labels or fluorescent labels) or, in the case of an enzymatic label, may catalyze chemical modification of a substrate compound which is detectable.

The methods for recombinantly producing the immune checkpoint modulator are conventional in the art. Typically such methods comprise (a) introducing the expression vector described herein into a suitable producer cell to produce a transfected or infected producer cell, (b) culturing in-vitro said transfected or infected producer cell under conditions suitable for its growth, (c) recovering the immune checkpoint modulator from the cell culture, and (d) optionally, purifying the recovered immune checkpoint modulator. In the context of the invention, producer cells include prokaryotic cells, lower eukaryotic cells such as yeast, and other eukaryotic cells such as insect cells, plant and mammalian (e.g. human or non-human) cells. Preferred E. coli cells include without limitation E. coli BL21 (Amersham Biosciences). Preferred yeast producer cells include without limitation S. cerevisiae, S. pombe, Pichia pastoris. Preferred mammalian producer cells include without limitation BHK-21 (baby hamster kidney), CV-1 (African monkey kidney cell line), COS (e.g. COS-7) cells, Chinese hamster ovary (CHO) cells, mouse NIH/3T3 cells, mouse NSO myeloma cells, HeLa cells, Vero cells, HEK293 cells and PERC.6 cells as well as the corresponding hybridoma cells.

The producer cells can be cultured in conventional fermentation bioreactors, flasks, and petri plates. Culturing can be carried out at a temperature, pH and oxygen content appropriate for a given host cell. No attempts to describe in detail the various methods known for the production of proteins in prokaryote and eukaryote cells will be made here. Production of the immune checkpoint modulator can be periplasmic, intracellular or preferably secreted outside the producer cell (e.g. in the culture medium).

If necessary, especially when the immune checkpoint modulator is not secreted outside the producer cell or where it is not secreted completely, it can be recovered by standard lysis procedures, including freeze thaw, sonication, mechanical disruption, use of lysing agents and the like. If secreted, it can be recovered directly from the culture medium.

The immune checkpoint modulator can then be purified by well-known purification methods including ammonium sulfate precipitation, acid extraction, gel electrophoresis, filtration and chromatographic methods (e.g. reverse phase, size exclusion, ion exchange, affinity, phosphocellulose, hydrophobic-interaction or hydroxylapatite chromatography, etc). The conditions and technology used to purify a particular protein will depend on factors such as net charge, molecular weight, hydrophobicity, hydrophilicity and will be apparent to those having skill in the art. Moreover, the level of purification will depend on the intended use. It is also understood that depending upon the producer cell, the immune checkpoint modulator proteins can have various glycosylation patterns, or may be non-glycosylated (e.g. when produced in bacteria) as described herein.

Desirably, the immune checkpoint modulator in use in the present invention is at least partially purified in the sense that it is substantially free of other antibodies having different antigenic specificities and/or other cellular material. Further, the immune checkpoint modulator may be formulated according to the conditions conventionally used in the art (e.g. WO2009/073569).

Another aspect of this invention pertains to the use of nucleic acid molecule(s) encoding the immune checkpoint modulator(s) described herein. For example, the immune checkpoint modulator may be delivered to the subject in the form of a vector expressing the one or more immune checkpoint modulator. Any of the vectors described herein can be used in this context.

Combination Therapy

The oncolytic virus and the one or more immune checkpoint modulator(s) may be administered together in a single composition or concurrently in separate compositions, optionally comprising a pharmaceutically acceptable vehicle in addition to a therapeutically effective amount of such active agent(s). Single composition encompasses the case where the oncolytic virus and said one or more immune checkpoint modulator(s) are mixed together (e.g. a mixture of the oncolytic virus and one or more antibodies or a mixture of the oncolytic virus and one or more vector(s) for expression of the one or more antibodies). Separate compositions of the oncolytic virus and said one or more immune checkpoint modulator(s) may be administered at the same time or sequentially, each once or several times (separately or in an interspersed manner) and via the same or different routes.

A "therapeutically effective amount" corresponds to the amount of each of the active agents (oncolytic virus and of the one or more immune check point modulator(s)) comprised in the combination or composition of the invention that is sufficient for producing one or more beneficial results. Such a therapeutically effective amount may vary as a function of various parameters, in particular the mode of administration; the disease state; the age and weight of the subject; the ability of the subject to respond to the treatment; kind of concurrent treatment; the frequency of treatment; and/or the need for prevention or therapy. When prophylactic use is concerned, the combination is administered at a dose sufficient to prevent or to delay the onset and/or establishment and/or relapse of a pathologic condition (e.g. a proliferative disease such as cancer), especially in a subject at risk. For "therapeutic" use, the combination of virus and immune checkpoint modulator(s) is administered to a subject diagnosed as having a pathological condition (e.g. a proliferative disease such as cancer) with the goal of treating the disease, eventually in association with one or more conventional therapeutic modalities. In particular, a therapeutically effective amount could be that amount necessary to cause an observable improvement of the clinical status over the baseline status or over the expected status if not treated, e.g. reduction in the tumor number; reduction in the tumor size, reduction in the number or extent of metastases, increase in the length of remission, stabilization (i.e. not worsening) of the state of disease, delay or slowing of disease progression or severity, amelioration or palliation of the disease state, prolonged survival, better response to the standard treatment, improvement of quality of life, reduced mortality, etc. A therapeutically effective amount could also be the amount necessary to cause the development of an effective non-specific (innate) and/or specific anti-tumor response. Typically, development of an immune response in particular T cell response can be evaluated in vitro, in suitable animal models or using biological samples collected from the subject. For example, techniques routinely used in laboratories (e.g. flow cytometry, histology) may be used to perform tumor surveillance. One may also use various available antibodies so as to identify different immune cell populations involved in anti-tumor response that are present in the treated subjects, such as cytotoxic T cells, activated cytotoxic T cells, natural killer cells and activated natural killer cells. An improvement of the clinical status can be easily assessed by any relevant clinical measurement typically used by physicians or other skilled healthcare staff.

The term "pharmaceutically acceptable vehicle" is intended to include any and all carriers, solvents, diluents, excipients, adjuvants, dispersion media, coatings, antibacterial and antifungal agents, absorption agents and the like compatible with administration in mammals and in particular human subjects.

Each of the oncolytic virus and the one or more immune check point modulator(s) or the composition thereof can independently be placed in a solvent or diluent appropriate for human or animal use. The solvent or diluent is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams&Wilkins).

In other embodiments, each of the oncolytic virus and the immune check point modulator composition(s) is suitably buffered for human use. Suitable buffers include without limitation phosphate buffer (e.g. PBS), bicarbonate buffer and/or Tris buffer capable of maintaining a physiological or slightly basic pH (e.g. from approximately pH 7 to approximately pH 9).

Each of the oncolytic virus and/or the immune check point modulator composition(s) may also contain other pharmaceutically acceptable excipients for providing desirable pharmaceutical or pharmacodynamic properties, including for example osmolarity, viscosity, clarity, colour, sterility, stability, rate of dissolution of the formulation, modifying or maintaining release or absorption into an the human or animal subject, promoting transport across the blood barrier or penetration in a particular organ.

Each of the oncolytic virus and of the immune check point modulator composition(s) can also comprise one or more adjuvant(s) capable of stimulating immunity (especially a T cell-mediated immunity) or facilitating infection of tumor cells upon administration, e.g. through toll-like receptors (TLR) such as TLR-7, TLR-8 and TLR-9, including without limitation alum, mineral oil emulsion such as, Freunds complete and incomplete (IFA), lipopolysaccharide or a derivative thereof (Ribi et al., 1986, Immunology and Immunopharmacology of Bacterial Endotoxins, Plenum Publ. Corp., NY, p 407-419), saponins such as QS21 (Sumino et al., 1998, J. Virol. 72: 4931; WO98/56415), imidazo-quinoline compounds such as Imiquimod (Suader, 2000, J. Am Acad Dermatol. 43:S6), S-27609 (Smorlesi, 2005, Gene Ther. 12: 1324) and related compounds such as those described in WO2007/147529, cytosine phosphate guanosine oligodeoxynucleotides such as CpG (Chu et al., 1997, J. Exp. Med. 186: 1623; Tritel et al., 2003, J. Immunol. 171: 2358) and cationic peptides such as IC-31 (Kritsch et al., 2005, J. Chromatogr Anal. Technol. Biomed. Life Sci. 822: 263-70).

In one embodiment, the oncolytic virus and the one or more immune checkpoint modulator(s) comprised in the combination of the present invention may be formulated with the goal of improving their stability in particular under the conditions of manufacture and long-term storage (i.e. for at least 6 months, with a preference for at least two years) at freezing (e.g. −70° C., −20° C.), refrigerated (e.g. 4° C.) or ambient temperatures. Various virus formulation are available in the art either in frozen, liquid form or lyophilized form (e.g. WO98/02522, WO01/66137, WO03/053463, WO2007/056847 and WO2008/114021, etc). Solid (e.g. dry powdered or lyophilized) compositions can be obtained by a process involving vacuum drying and freeze-drying. For illustrative purposes, sterile histidine, acetate citrate or phosphate buffers saline containing surfactant such as polysorbate 80 and stabilizers such as sucrose or mannitol are adapted to the preservation of recombinant antibodies and buffered formulations including NaCl and/or sugar are particularly adapted to the preservation of viruses (e.g. Tris 10 mM pH 8 with saccharose 5% (W/V), Sodium glutamate 10 mM, and NaCl 50 mM or phosphate-buffered saline with glycerol (10%) and NaCl).

In certain embodiments, the immune checkpoint modulator can be formulated to ensure proper distribution or a delayed release in vivo. For example, it can be formulated in liposomes. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g. J. R. Robinson in "Sustained and Controlled Release Drug Delivery Systems", ed., Marcel Dekker, Inc., New York, 1978.

The appropriate dosage of oncolytic virus and immune checkpoint modulator(s) can be adapted as a function of various parameters and may be routinely determined by a practitioner in the light of the relevant circumstances. Suitable dosage of the immune checkpoint modulator(s) varies from about 0.01 mg/kg to about 50 mg/kg, advantageously from about 0.1 mg/kg to about 30 mg/kg, desirably from about 0.5 mg/kg to about 25 mg/kg, preferably from about 1 mg/kg to about 20 mg/kg, more preferably from about 2 mg/kg to about 15 mg/kg, with a specific preference for doses from about 3 mg/kg to about 10 mg/kg (e.g. 3 mg/kg, 4 mg/kg, 5 mg/kg, 6 mg/kg, 7 mg/kg, 8 mg/kg, 9 mg/kg or 10 mg/kg) when used systemically. However, doses reduced by a factor of 10 to 100 may be considered for local intratumoral injection(s) of the immune checkpoint modulator(s). Suitable dosage for the oncolytic virus varies from approximately $10^5$ to approximately $10^{13}$ vp (viral particles), iu (infectious unit) or pfu (plaque-forming units) depending on the virus and the quantitative technique used. As a general guidance, vaccinia virus doses from approximately $10^5$ to approximately $10^{13}$ pfu are suitable, preferably from approximately $10^6$ pfu to approximately $10^{11}$ pfu, more preferably from approximately $10^7$ pfu to approximately $5 \times 10^9$ pfu; doses of approximately $10^8$ pfu to approximately $10^9$ pfu being particularly preferred (e.g. dose of $10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$ or $10^9$ pfu) especially for human use. On the same line, doses reduced by a factor of 10 to 100 may be considered for local intratumoral injection(s) of the oncolytic virus. Individual doses of $10^6$ to $5 \times 10^{12}$ vp are particularly appropriate for oncolytic adenovirus, preferably from $10^7$ to $10^{12}$ vp, more preferably from $10^8$ to $5 \times 10^{11}$ vp. The quantity of virus present in a sample can be determined by routine titration techniques, e.g. by counting the number of plaques following infection of permissive cells using permissive cells (e.g. BHK-21 or CEF), immunostaining (e.g. using anti-virus antibodies; Carol) et al., 1997, Virology 238: 198-211), by measuring the A260 absorbance (vp titers), or still by quantitative immunofluorescence (iu titers).

Administration

The oncolytic virus and/or the immune check point modulator may be administered together or separately to the subject and in a single dose or multiple doses. Administrations may be performed by the same or different routes and may take place at the same site or at alternative sites.

Any of the conventional administration routes are applicable in the context of the invention including parenteral, topical or mucosal routes, for each of the active agents comprised in the combination of the invention. Parenteral routes are intended for administration as an injection or infusion and encompass systemic as well as local routes. Common parenteral injection types are intravenous (into a vein), intra-arterial (into an artery), intradermal (into the dermis), subcutaneous (under the skin), intramuscular (into muscle) and intratumoral (into a tumor or at its close proximity). Infusions typically are given by intravenous route. Mucosal administrations include without limitation oral/alimentary, intranasal, intratracheal, intrapulmonary, intravaginal or intra-rectal route. Topical administration can also be performed using transdermal means (e.g. patch and the like). Administrations may use conventional syringes and needles (e.g. Quadrafuse injection needles) or any compound or device available in the art capable of facilitating or improving delivery of the active agent(s) in the subject. Preferred routes of administration for the immune checkpoint modulator(s) include intravenous (e.g. intravenous injection or infusion), intratumoral and intraperitoneal. Transdermal patches may also be envisaged. Preferred routes of administration for the oncolytic virus include intravenous and intratumoral. Local intratumoral inoculations of the oncolytic virus could be advantageously combined with local intratumoral injections of the immune checkpoint modulator(s), concomitantly or with different scheduling to expect optimal abscopal effects on distant metastases or tumor lesions. This may also permit to lower effective amounts of each product and also to reduce unwanted side effects.

In a preferred embodiment, the oncolytic virus and the one or more immune checkpoint modulator(s) can be administered sequentially, such as the oncolytic virus being administered first and the immune checkpoint modulator(s) second, or vise-versa (immune checkpoint modulator(s) being administered first and oncolytic virus second). If more than one immune checkpoint modulator(s) is used (e.g. anti-PD-1 and anti-CTLA-4 antibodies), they may be administered simultaneously or sequentially, in which case the dosage of each antibody administered falls within the ranges indicated herein. Furthermore, if more than one dose of the combination therapy is administered sequentially, the order of the sequential administration can be reversed or kept in the same order at each time point of administration. Moreover, sequential administrations may be combined with concurrent administrations. It is also possible to proceed via sequential cycles of administrations that are repeated after a rest period. Intervals between each administration can be from several hours to one year (e.g. 24 h, 48 h, 72 h, weekly, every two weeks, monthly or yearly). Intervals can also be irregular (e.g. following the measurement of monoclonal antibodies in the patient blood levels). The doses can vary for each administration within the range described above.

In the context of the invention, the oncolytic virus may be administered once or several time (e.g. 2, 3, 4, 5, 6, 7 or 8 times etc) at a dose within the range of from $10^7$ to $5 \times 10^9$ pfu. The time interval between each virus administration can vary from approximately 1 day to approximately 8 weeks, advantageously from approximately 2 days to approximately 6 weeks, preferably from approximately 3 days to approximately 4 weeks and even more preferably from approximately 1 week to approximately 3 weeks. In combination, the immune check point modulator(s) is/are administered once or several time (e.g. 2, 3, 4, 5, 6, 7 or 8 times etc) at a dose within the range of from 2 mg/kg to 15 mg/kg. The time interval between each administration of the immune check point modulator(s) can vary from approximately 1 day to approximately 8 weeks, advantageously from approximately 2 days to approximately 6 weeks, preferably from approximately 3 days to approximately 4 weeks and even more preferably from approximately 3 days to approximately 3 weeks. For illustrative purpose, a preferred administration schedule for ipilimumab is 3 mg/kg as an intravenous infusion every 3 weeks for a total of four doses. In some embodiments, two or more monoclonal antibodies with different binding specificities are administered simultaneously, in which case the dosage of each antibody administered falls within the ranges indicated. In a preferred embodiment, the oncolytic virus and the immune checkpoint modulator(s) are administered sequentially (separately or interspersed), with a specific preference for the virus starting first followed by the immune checkpoint modulator(s). The period of time between the first administration of the oncolytic virus and the first administration of the immune check point modulator(s) may vary from approximately several hours (at least 6 hours) to several week(s). In a preferred embodiment, the method of the present invention comprises at least one administration of the oncolytic virus before starting administration of the immune checkpoint modulator(s), with a specific preference for at least 2 viral administrations followed by 2 to 5 administrations of the immune check point modulator(s) (e.g. 1, 2, 3, 4, 5, 6, 7, 8, 9, 10, 11, 12, 13 or 14 days separating the second viral administration from the first immune checkpoint modulator administration). Another preferred therapeutic scheme involves from 2 to 5 (e.g. 3) intravenous or intratumoral administrations of $10^8$ or $10^9$ pfu of oncolytic vaccinia virus at approximately 1 or 2 weeks interval followed by or interspersed with 2 to 5 (e.g. 3 or 4) intravenous administrations of 3 to 10 mg/kg of anti-immune checkpoint antibody(ies)(s) every 2 or 3 weeks.

The present invention also relates to a method for treating a proliferative disease such as cancer comprising administering an oncolytic virus and one or more immune checkpoint modulator(s) to a subject in need thereof. In particular, the combination of an oncolytic virus and one or more immune checkpoint modulator(s) as described herein is for use for treating a proliferative disease and, especially, for treating a cancer in a subject having or at risk of having a cancer.

The present invention also relates to a method for inhibiting tumor cell growth in vivo comprising administering an oncolytic virus and one or more immune checkpoint modulator(s) to a subject in need thereof. In particular, the combination of an oncolytic virus and one or more immune checkpoint modulator(s) as described herein is for use for increasing lysis of dividing cells.

The present invention also relates to a method for enhancing an immune response to tumor cells comprising administering an oncolytic virus and one or more immune checkpoint modulator(s) to a subject in need thereof. In particular, the combination of an oncolytic virus and one or more immune checkpoint modulator(s) as described herein is for use for increasing the number and/or functionality of CD8+ T lymphocytes and especially of tumor-infiltrating CD8+ T lymphocytes.

The present invention also relates to an allogeneic tumor cell line infected ex vivo with the oncolytic virus described herein in combination with the one or more immune checkpoint modulator(s) described herein as well as to a method for ex vivo treating a proliferative disease such as cancer comprising administering said allogenic tumor cell line infected with said oncolytic virus followed by administering said one or more immune checkpoint modulator(s) to a subject in need thereof, so as to activate the immunity induced by said infected allogenic tumor cell line in said subject.

Examples of proliferative diseases that may be treated using the combination and methods of the invention include bone cancer, liver cancer, pancreatic cancer, stomach cancer, colon cancer, cancer of the esophagus, oro-pharyngeal cancer, lung cancer, cancer of the head or neck, skin cancer, melanoma, uterine cancer, cervix cancer, ovarian cancer, breast cancer, rectal cancer, cancer of the anal region, prostate cancer, lymphoma, cancer of the endocrine system, cancer of the thyroid gland, sarcoma of soft tissue, chronic or acute leukemias, cancer of the bladder, renal cancer, neoplasm of the central nervous system (CNS), glioma, etc. The present invention is also useful for treatment of metastatic cancers, especially metastatic cancers that express PD-L1 (Iwai et al., 2005, Int. Immunol. 17: 133-44). Preferred cancers that may be treated using the combination therapy according to the invention include cancers typically responsive to immunotherapy. Non-limiting examples of preferred cancers for treatment include melanoma (e.g. metastatic malignant melanoma), renal cancer (e.g. clear cell carcinoma), prostate cancer (e.g. hormone refractory prostate adenocarcinoma), breast cancer, colorectal cancer, lung cancer (e.g. non-small cell lung cancer) and liver cancer (e.g. hepatocarcinoma).

According to an advantageous embodiment, especially when the oncolytic virus is armed with a suicide gene, the combination therapy or methods according to the present invention may comprise an additional step in which pharmaceutically acceptable quantities of a prodrug, advantageously an analog of cytosine, in particular 5-FC, are administered to the subject. By way of illustration, it is possible to use a dose of from 50 to 500 mg/kg/day, with a dose of 200 mg/kg/day or of 100 mg/kg/day being preferred. Within the context of the present invention, the prodrug is administered in accordance with standard practice (e.g. per os, systematically, etc). Preferably, the administration taking place subsequent to the administration of the oncolytic virus, preferably at least 3 days, more preferably at least 4 days and even more preferably at least 7 days after the administration of the virus. The oral route is preferred. It is possible to administer a single dose of prodrug or doses which are repeated for a time which is sufficiently long to enable the toxic metabolite to be produced within the host organism or cell.

The combination or method according to the invention can be associated with one or more substances effective in anticancer therapy. Among pharmaceutical substances effective in anticancer therapy which may be used in association or in combination with the compositions according to the invention, there may be mentioned more specifically:

- alkylating agents such as e.g. mitomycin C, cyclophosphamide, busulfan, ifosfamide, isosfamide, melphalan, hexamethylmelamine, thiotepa, chlorambucil, or dacarbazine;
- antimetabolites such as, e.g. gemcitabine, capecitabine, 5-fluorouracil, cytarabine, 2-fluorodeoxy cytidine, methotrexate, idatrexate, tomudex or trimetrexate;
- topoisomerase II inhibitors such as, e.g. doxorubicin, epirubicin, etoposide, teniposide or mitoxantrone;
- topoisomerase I inhibitors such as, e.g. irinotecan (CPT-11), 7-ethyl-10-hydroxy-camptothecin (SN-38) or topotecan;
- antimitotic drugs such as, e.g., paclitaxel, docetaxel, vinblastine, vincristine or vinorelbine;
- platinum derivatives such as, e.g., cisplatin, oxaliplatin, spiroplatinum or carboplatinum;
- inhibitors of tyrosine kinase receptors such as sunitinib (Pfizer) and sorafenib (Bayer); and
- anti-neoplastic antibodies.

The combination or method according to the invention may also be used in association with one or more other agents including but not limited to immunomodulatory agents such as, e.g. alpha, beta or gamma interferon, interleukin (in particular IL-2, IL-6, IL-10 or IL-12) or tumor necrosis factor; agents that affect the regulation of cell surface receptors such as, e.g. inhibitors of Epidermal Growth Factor Receptor (in particular cetuximab, panitumumab, zalutumumab, nimotuzumab, matuzumab, gefitinib, erlotinib or lapatinib) or inhibitors of Human Epidermal Growth Factor Receptor-2 (in particular trastuzumab); and agents that affect angiogenesis such as, e.g. inhibitor of Vascular Endothelial Growth Factor (in particular bevacizumab or ranibizumab).

Such substances effective in anticancer therapy may be administered to the subject sequentially or concomitantly with the combination or method according to the invention.

Alternatively or in combination, the combination or method according to the invention can also be used in association with radiotherapy.

The present invention also provides kits including the active agent(s) of the combination of the invention in kit form. In one embodiment, a kit includes at least an oncolytic virus as discussed herein in one container (e.g., in a sterile glass or plastic vial), and one or more immune checkpoint modulator(s) as described herein in another container (e.g., in a sterile glass or plastic vial). A preferred kit comprises an oncolytic vaccinia virus (e.g. a vaccinia virus defective for both TK and RR activities armed with a suicide gene) and an immune checkpoint modulator(s) which specifically binds CTLA-4 (e.g. an anti-CTLA-4 antibody, such as ipilimumab). Another preferred kit comprises an oncolytic vaccinia virus (e.g. a vaccinia virus defective for both TK and RR activities armed with a suicide gene) and an immune checkpoint modulator(s) which specifically binds PD-1 (e.g., an anti-PD-1 antibody, such as nivolumab or lanbrolizumab). Another preferred kit comprises an oncolytic vaccinia virus (e.g. a vaccinia virus defective for both TK and RR activities armed with a suicide gene) and an immune checkpoint modulator(s) which specifically binds PD-L1 (e.g., an anti-PD-L1 antibody, such as MPDL3280A or BMS936559). Optionally, the kit can include a device for performing the administration of the active agents. The kit can also include a package insert including information concerning the compositions or individual component and dosage forms in the kit.

EXAMPLES

Figure 1A:
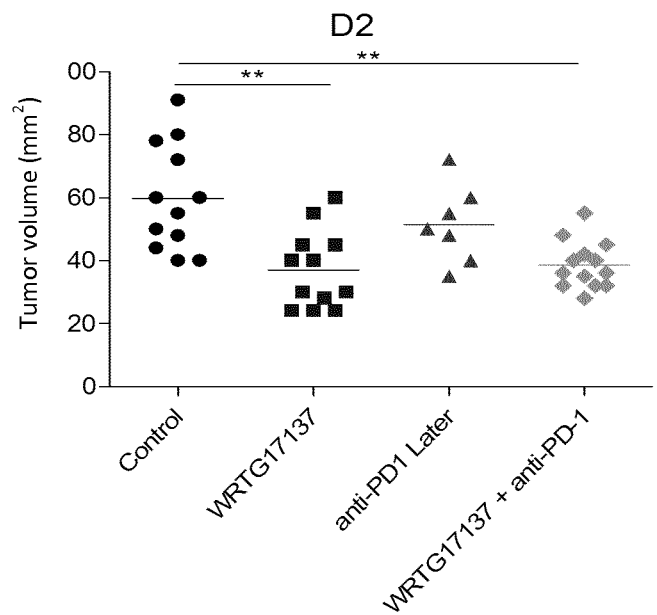
FIGS. 1 A, B and C illustrate the growth of MCA205 tumors implanted in mice at different time points (D2, D13 and D20, respectively) treated with 2 intratumoral injections of $10^7$ pfu of WRTG17137 at day 0 and 3 and 3 intraperitoneal injections of 250 μg of anti-PD-1 antibody at day 6, 9 and 12.

We set out to combine immune checkpoint blocking approaches with oncolytic vaccinia vectors. Virus replication in tumors would lead to cell death, destruction of the tumor and liberation of tumor antigen. Combination of oncolytic viruses with anti-immune checkpoint inhibitors should release the brakes from T cell generation and resulting tumor-specific T-cells. Preclinical evidence for synergistic effects of immune checkpoint blockers combined with viral vectors was to be demonstrated in mouse tumor models. This implies the use of i) murine-specific anti-immune check point antibodies and ii) an oncolytic poxvirus capable of infecting murine cells with a higher efficacy.

The oncolytic virus chosen for these studies (WRTG17137) is a vaccinia virus (VV) Western Reserve (WR) strain defective for thymidine kinase (TK) (locus J2R) and $RR^-$ (locus 14L) rendering the virus non-replicative in healthy (non-dividing) cells. In contrast, the VV $TK^-RR^-$ is supposed to selectively and efficiently replicate in tumor cells. It is armed with the chimeric yeast-derived gene FCU-1, an enzyme turning prodrug 5-fluorocytosine (5-FC) in the toxic anabolites 5-fluorouracil (5-FU) and 5-fluorouridine-5'monophosphate (Erbs et al., 2000, Cancer Res., 60(14): 3813-22).

Two immune checkpoint modulators, namely anti-PD-1 and anti-CTLA4 monoclonal antibodies, were individually tested in combination with WRTG17137.

Combination of Oncolytic VV with Anti-PD-1 MAb

It was first chosen to target the immune checkpoint blocker murine PD-1 (mPD-1) with an appropriate antibody. The rat anti mPD-1 antibody RMP1-14 (BioXcell) was chosen as anti mPD-1. This antibody was shown to block the interaction of mPD1 with its ligands (Yamazaki et al., 2005, J. Immunol. 175(3): 1586-92).

The combination of mPD-1 inhibitors (commercial clone RMP1-14) with the oncolytic virus WRTG17137 was tested in vivo in the MCA205 (Shu and Rosenberg, 1985, Cancer Res. 45(4): 1657-62) mouse model. Various schedules of administration were experimented.

In a first setting, C57BL/6 mice were subcutaneously injected with $8\times10^5$ MCA205 tumor cells. Day 7 after tumor cell injection, 250 μg anti mPD1 antibody RMP1-14 or its isotype control 2A3 were injected intraperitoneal (ip) at days 0, 3 and 6. Virus WRTG17137 ($1\times10^7$ pfu) was then injected intratumorally (it) twice at days 7 and 10. Four groups of 13 mice were tested, a control group receiving isotype control (3 ip injections at days 0, 3 and 6), a group of mice treated with the anti-PD-1 mAb (3 ip injections at days 0, 3 and 6), a group of mice treated with the oncolytic virus (2 it injections at days 7 and 10) and the fourth group receiving both the anti-PD-1 mAb (3 ip injections at days 0, 3 and 6) followed one day after the last antibody injection by 2 injections of WRTG17137 (2 it injections at days 7 and 10). Tumor progression and mice survival were followed over 40 days.

As expected, tumor increased in size very rapidly in control group whereas the tumor growth was delayed in all the three other groups within the same extend although a slight improvement was seen in the group receiving both mPD-1 antibody and the oncolytic virus. Results of survival are on the same line with a 50% survival obtained at 16, 23, 24 and 26 days, respectively in control group, antibody group, WRTG17137-treated group and antibody+WRTG17137-treated group.

In the second setting, C57BL/6 mice were subcutaneously injected with $8 \times 10^5$ MCA205 tumor cells as before and the animals were divided in four groups of 13 mice, respectively a control group receiving isotype control (3 ip injections at days 6, 9 and 12), a group of mice treated with the oncolytic virus (2 it injections at days 0 and 3 of $1 \times 10^7$ pfu WRTG17137), a group of mice treated with the anti-PD-1 mAb (3 ip injections at days 6, 9 and 12 of 250 µg anti mPD1 antibody RMP1-14), and the fourth group receiving both the virus (at days 0 and 3) followed three days after by the antibody (3 ip injections every three days, i.e. at days 6, 9 and 12). Tumor progression and survival were followed over 40 days.

Figure 1B:
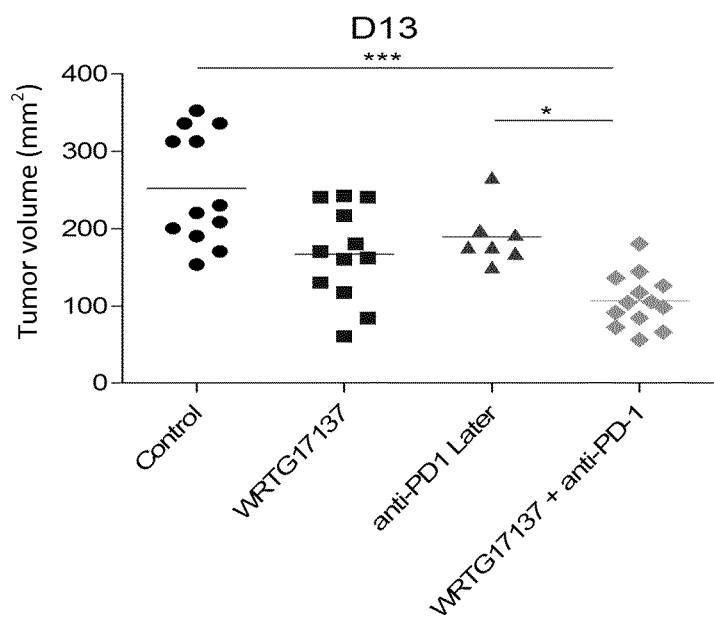
Figure 1C:
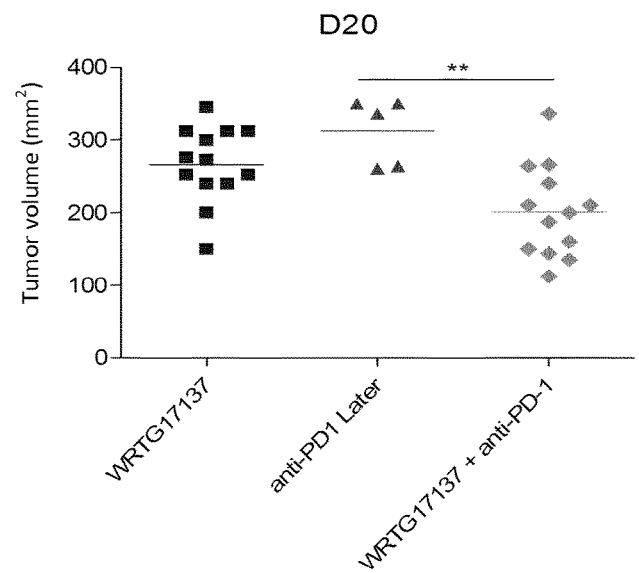

As expected, tumors increased in size very rapidly in control group whereas the tumor growth was delayed in all the three other groups. However, as illustrated in FIG. 1, tumor growth is delayed within the same extend in the groups treated with only one component (mPD-1 antibody or oncolytic virus) and the slowdown is more pronounced in the group receiving both mPD-1 antibody and the oncolytic virus, especially at time point D13 and D20.

Figure 2:
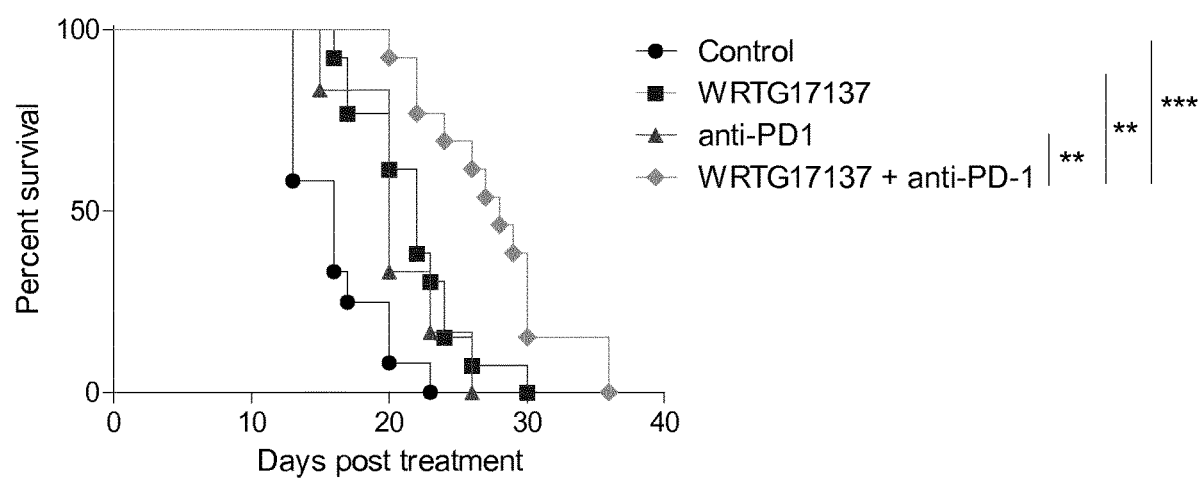
FIG. 2 illustrates the percent of survival in mice implanted with $8\times10^5$ MCA205 tumor cells and treated with 2 intratumoral injections of WRTG17137 at day 0 and 3 and 3 intraperitoneal injections of anti-PD-1 antibody at day 6, 9 and 12.

As illustrated in FIG. 2, 50% survival is obtained at day 16 in the control group. An increase of survival was observed due to WRTG17137 injection (50% survival at day 22) or due to mPD-1 injection (50% survival at day 20). Survival was further increased after administration of WRTG17137 followed by antibody (50% survival measured at day 28).

Combination of Anti-CTLA4 Inhibitors

Combination of anti-CTLA-4 antibody (commercial clone 9D9) with the oncolytic virus WRTG17137 was tested in vivo in the MCA205 mouse model. Various schedules of administration were experimented.

In a first setting, C57BL/6 mice were subcutaneously injected with $8 \times 10^5$ tumor cells (MCA205). Day 7 after tumor cell injection, 100 µg anti CTLA-4 antibody 9D9 (BioXcell) were injected ip at days 0, 3 and 6. Virus WRTG17137 ($1 \times 10^7$ pfu) was injected intratumorally twice at days 7 and 10. Four groups of 6 mice were tested, respectively a control group receiving isotype control MCP-11 (3 ip injections at days 0, 3 and 6), a group of mice treated with the anti-CTLA-4 mAb (3 ip injections at days 0, 3 and 6), a group treated with the oncolytic virus (2 it injections at days 7 and 10) and the fourth group receiving both the anti-CTLA-4 antibody (3 ip injections at days 0, 3 and 6) followed one day after the last antibody injection by 2 injections of WRTG17137 (2 it injections at days 7 and 10). Tumor progression and mice survival were followed over 35 days As expected, tumor increased in size very rapidly in control group whereas the tumor growth was delayed in all the three other groups within approximately the same extend.

In the second setting, mice were subcutaneously injected with $8 \times 10^5$ MCA tumor cells as before. Four groups of 6 mice were tested, a control group receiving the isotype control MCP-11 (3 ip injections at days 0, 3 and 6), a group of mice treated with the oncolytic virus (2 it injections at days 0 and 3 of $1 \times 10^7$ pfu WRTG17137), a group of mice treated with 100 µg of anti-CTLA-4 mAb 9D9 (3 ip injections at days 6, 9 and 12), and the fourth group receiving both the virus (at days 0 and 3) followed three days after by the anti-CTLA-4 antibody (3 ip injections every three days, i.e. at days 6, 9 and 12). Tumor progression and survival were followed over 35 days.

Figure 3A:
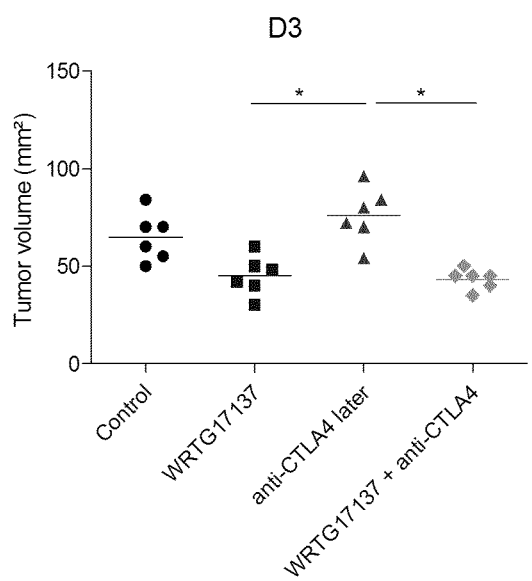
FIGS. 3 A, B and C illustrate the growth of MCA205 tumors implanted in mice at different time points (D3, D8 and D13, respectively) treated with 2 intratumoral injections of $10^7$ pfu of WRTG17137 at day 0 and 3 and 3 intraperitoneal injections of 100 μg of anti-CTLA4 antibody at day 6, 9 and 12.
Figure 3B:
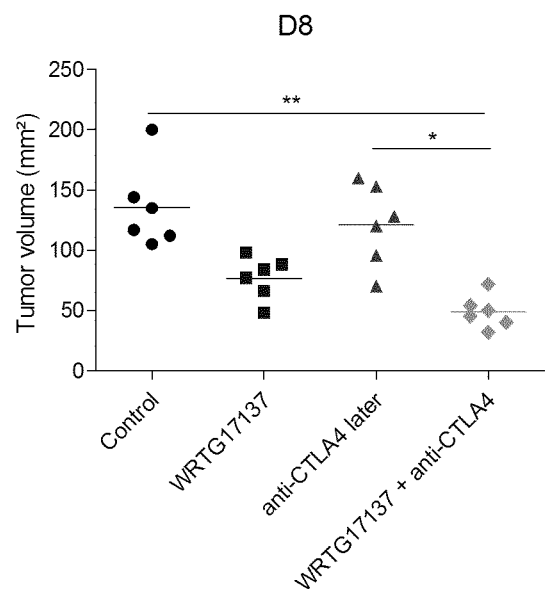
Figure 3C:
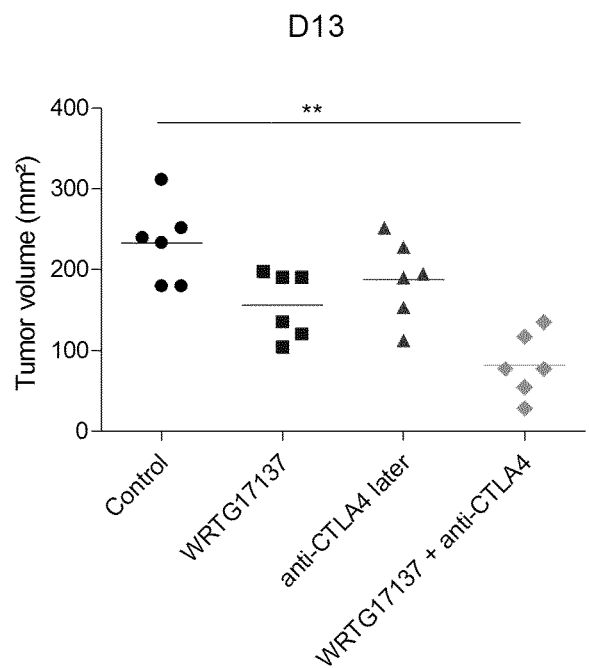

As expected, tumors increased in size very rapidly in control groups. Tumor growth was delayed in all the three other groups. However, as illustrated in FIG. 3, the tumor volume is decreased in the groups treated with only one component (anti-CTLA-4 antibody or oncolytic virus), the slowdown is much more pronounced in the group receiving both antiCTLA4 antibody and the oncolytic virus.

Figure 4:
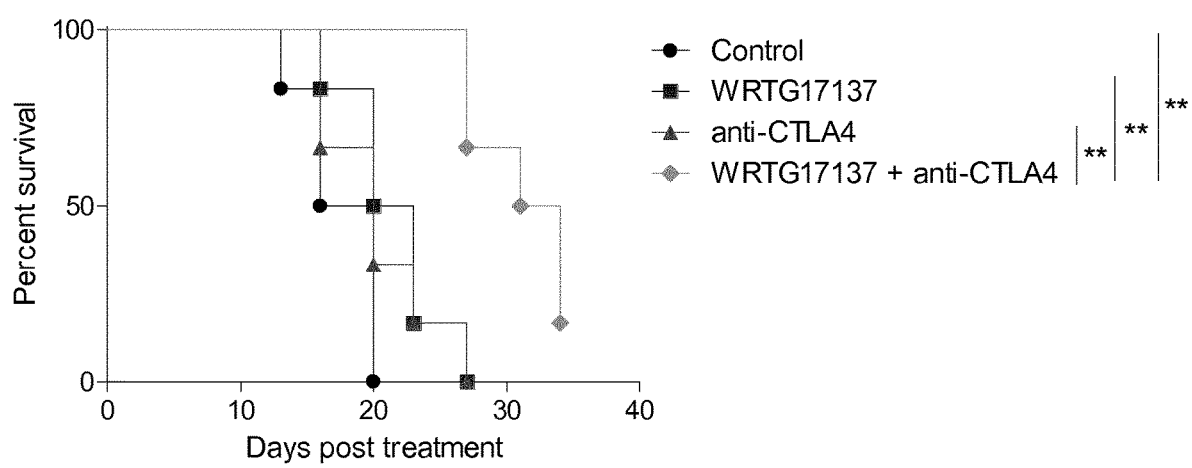
FIG. 4 illustrates the percent of survival in mice implanted with $8\times10^5$ tumor cells and treated with 2 intratumoral injections of WRTG17137 at day 0 and 3 and 3 intraperitoneal injections of anti-CTLA-4 antibody at day 6, 9 and 12.

As illustrated in FIG. 4, 50% survival is obtained at day 18 in the control group. An increase of survival was observed due to WRTG17137 injection (50% survival at day 21) or due to anti CTLA-4 antibody injection (50% survival at day 20). Survival was further increased after administration of WRTG17137 followed by antibody (50% survival measured at day 32).

Dose Effects

The same experiment as before was carried out with varying doses of virus. Four groups of six mice were treated after tumor implantation ($8 \times 10^5$ MCA tumor cells). A control group received formulation buffer in place of virus and isotype control in place of the antibody. A second group was treated with $10^5$, $10^6$ or $10^7$ pfu of WRTG17137 (2 it injections at days 0 and 3) and a third one with the anti-PD-1 mAb (3 ip injections at days 6, 9 and 12 of 250 µg anti mPD1 antibody RMP1-14). A fourth group received both the virus ($10^5$, $10^6$ or $10^7$ pfu at days 0 and 3) followed three days after by the antibody (3 ip injections every three days, i.e. at days 6, 9 and 12). Tumor progression was followed over 15 days.

Figure 5:
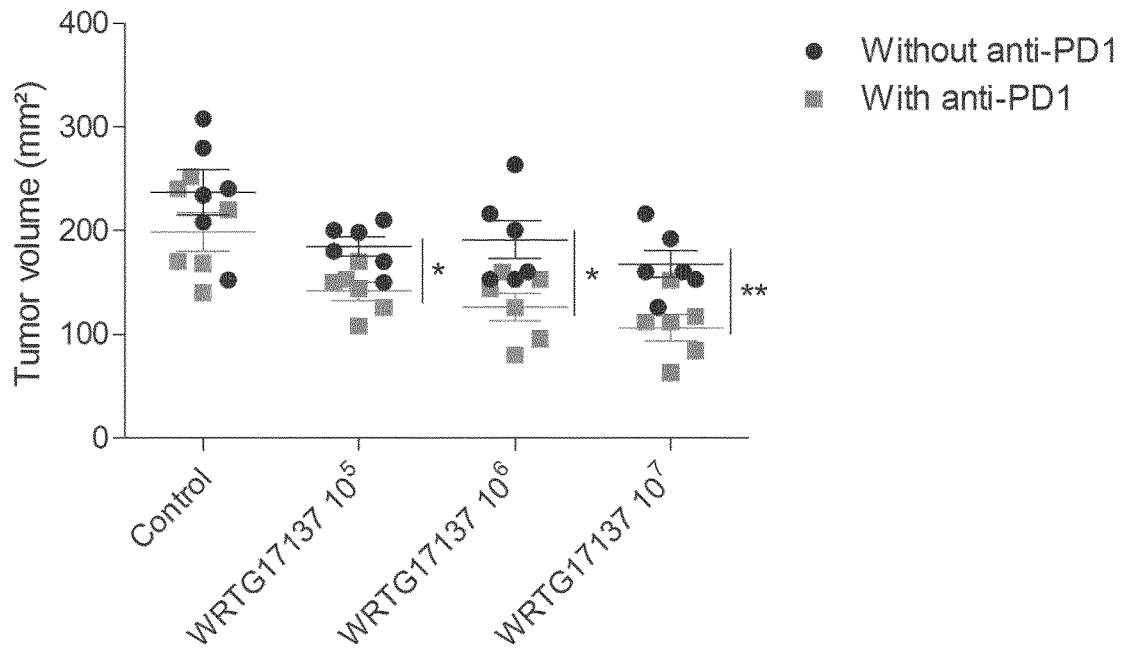
FIGS. 5 A and B illustrate the growth of MCA205 tumors implanted in mice treated with 2 intratumoral injections of increasing doses of WRTG17137 ($10^5$, $10^6$ or $10^7$ pfu) at day 0 and 3 and 3 intraperitoneal injections of 250 μg of anti-PD-1 antibody at day 6, 9 and 12. Tumor progression is measured at days 12 and 14. Black and round points represent tumor progression in mice treated with the virus only and grey and square points represent tumor progression in mice treated with the virus and the anti-PD1 antibody.
Figure 5:
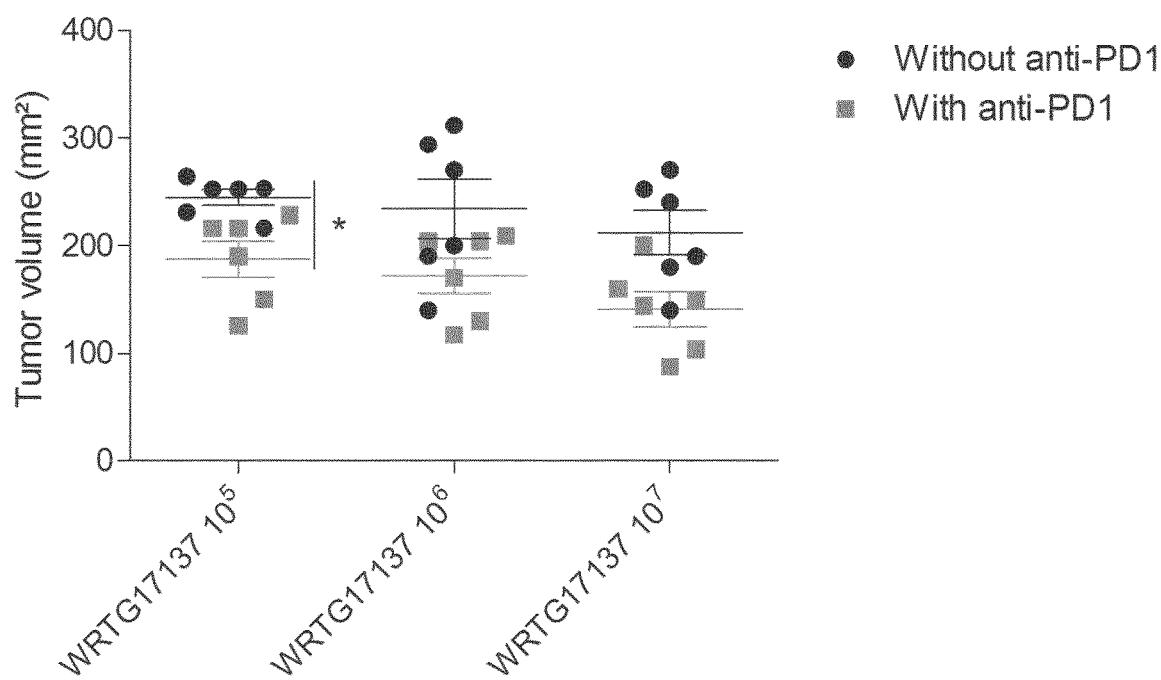

FIG. 5 illustrates the tumor progression observed in mice treated with the same dose of virus alone (black and round points) or in combination with the anti-PD-1 (grey and square points) 12 and 14 days following the first virus injection. Whatever the virus dose injected into the tumor, tumor growth is delayed in mice treated with the combination of virus+anti-PD-1 as compared to that measured in mice treated with the oncolytic virus only.

These results illustrate the therapeutic and synergistic anti-tumor activity of the combination of the invention especially when virus is administered first before the immune check point modulator.

Variation of the Time Interval Between Virus and Antibody Administrations

Anti-PD1 Antibody Combination

Six weeks old female C57BL/6 mice were injected subcutaneously (sc) into the right flanks with $8 \times 10^5$ MCA205 tumor cells. At day 0 (D0), when tumor volumes reached 40-60 mm$^2$, the animals were randomized and divided in 11 groups of 6 mice. A control group receiving buffer (2 it injections at days 0 and 3), a group of mice treated with the oncolytic virus (2 it injections at days 0 and 3 of $1 \times 10^7$ pfu WRTG17137), a group receiving both the virus (at days 0 and 3) and the isotype control (3 ip injections at days 6, 9 and 12), a group of mice treated with both the virus (at days 0 and 3) and the anti-PD-1 mAb (3 ip injections at days 4, 7 and 10 of 250 µg anti mPD1 antibody clone RMP1-14), a group of mice treated with both the virus (at days 0 and 3)

and the anti-PD-1 mAb (3 ip injections at days 6, 9 and 12 of 250 µg anti mPD1 antibody clone RMP1-14), a group of mice treated with both the virus (at days 0 and 3) and the anti-PD-1 mAb (3 ip injections at days 8, 11 and 14 of 250 µg anti mPD1 antibody clone RMP1-14), a group of mice treated with both the virus (at days 0 and 3) and the anti-PD-1 mAb (3 ip injections at days 10, 13 and 16 of 250 µg anti mPD1 antibody clone RMP1-14), a group of mice receiving both the virus (at days 0 and 3) and the anti-PD-1 mAb (3 ip injections at days 4, 7 and 10 of 100 µg anti mPD1 antibody clone RMP1-14), a group of mice receiving both the virus (at days 0 and 3) and the anti-PD-1 mAb (3 ip injections at days 6, 9 and 12 of 100 µg anti mPD1 antibody clone RMP1-14), a group of mice receiving both the virus (at days 0 and 3) and the anti-PD-1 mAb (3 ip injections at days 8, 11 and 14 of 100 µg anti mPD1 antibody clone RMP1-14), and a group of mice receiving both the virus (at days 0 and 3) and the anti-PD-1 mAb (3 ip injections at days 10, 13 and 16 of 100 µg anti mPD1 antibody clone RMP1-14). Tumor progression and survival were followed over time.

Figure 6:
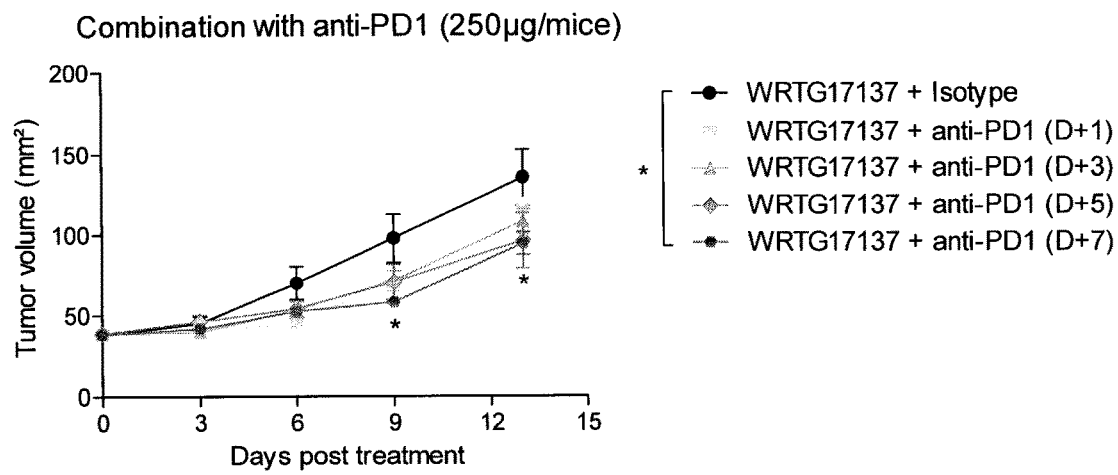
FIG. 6 illustrates the growth of MCA205 tumors implanted in mice treated with 2 intratumoral injections of $10^7$ pfu of WRTG17137 at day 0 and 3 and 3 intraperitoneal injections of 250 μg of anti-PD-1 antibody or isotype control, the first antibody injection being 1, 3, 5 or 7 days after the second virus injection. Tumor progression is measured over time. Black round points represent tumor progression in mice treated with the virus and isotype control whereas grey square, triangle, diamond and hexagon shaped points represent tumor progression in mice treated with the virus and the anti-PD1 antibody 1, 3, 5 and 7 days after the second virus injection.

As shown in FIG. 6, tumor growth is delayed in mice treated with the combination of virus and anti-PD-1 (250 µg/mice) as compared to that measured in mice treated with the oncolytic virus and the isotype antibody. The more time there is between the administrations of the virus and those of antibody, the more tumor growth is controlled. Statistical differences between the control group and the virus+anti-PD-1 group (D+7, that is 3 ip injections at days 10, 13 and 16 of 250 µg anti mPD1 antibody clone RMP1-14) were seen at 9 and 13 days post treatment. The same tendency was observed in the groups of animals treated with the combination of WRTG17137 ($1\times10^7$ pfu/mice) and anti-PD-1 (100 µg/mice) although without any statistical differences with respect to the control group ($1\times10^7$ pfu/mice+100 µg isotype/mice).

Anti-CTLA-4 Antibody Combination

Six weeks old female C57BL/6 mice were injected subcutaneously (sc) into the right flanks with $8\times10^5$ MCA205 tumor cells. At day 0 (DO), when tumor volumes reached 40-60 mm$^2$, the animals were randomized and divided in 11 groups of 6 mice. A control group receiving buffer (2 it injections at days 0 and 3), a group of mice treated with the oncolytic virus (2 it injections at days 0 and 3 of $1\times10^7$ pfu WRTG17137), a group receiving both the virus (at days 0 and 3) and the isotype control (3 ip injections at days 6, 9 and 12), a group of mice treated with both the virus (at days 0 and 3) and the anti-CTLA4 mAb (3 ip injections at days 4, 7 and 10 of 100 µg anti mCTLA4 antibody clone 9D9), a group of mice treated with both the virus (at days 0 and 3) and the anti-CTLA4 mAb (3 ip injections at days 6, 9 and 12 of 100 µg anti mCTLA4 antibody clone 9D9), a group of mice treated with both the virus (at days 0 and 3) and the anti-CTLA4 mAb (3 ip injections at days 8, 11 and 14 of 100 µg anti m CTLA4 antibody clone 9D9), a group of mice treated with both the virus (at days 0 and 3) and the anti-CTLA4 mAb (3 ip injections at days 10, 13 and 16 of 100 µg anti-mCTLA4 antibody clone 9D9), a group of mice receiving both the virus (at days 0 and 3) and the anti-CTLA4 mAb (3 ip injections at days 4, 7 and 10 of 50 µg anti-mCTLA4 antibody clone 9D9), a group of mice receiving both the virus (at days 0 and 3) and the anti-CTLA4 mAb (3 ip injections at days 6, 9 and 12 of 50 µg anti-mCTLA4 antibody clone 9D9), a group of mice receiving both the virus (at days 0 and 3) and the anti-CTLA4 mAb (3 ip injections at days 8, 11 and 14 of 50 µg anti-mCTLA4 antibody clone 9D9), and a group of mice receiving both the virus (at days 0 and 3) and the anti-CTLA4 mAb (3 ip injections at days 10, 13 and 16 of 50 µg anti-mCTLA4 antibody clone 9D9). Tumor progression and survival were followed over time.

Figure 7:
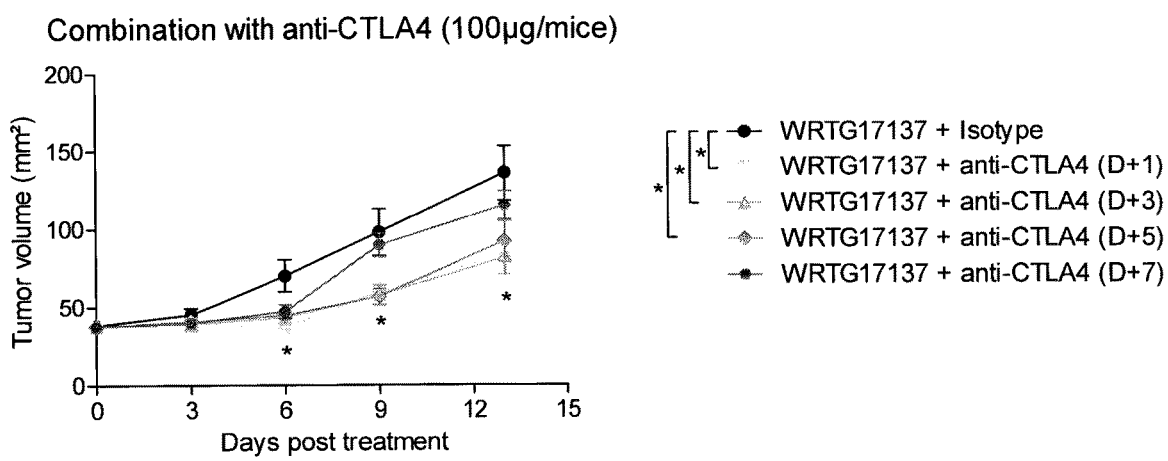
FIG. 7 illustrates the growth of MCA205 tumors implanted in mice treated with 2 intratumoral injections of $10^7$ pfu of WRTG17137 at day 0 and 3 and 3 intraperitoneal injections of 100 μg of anti-CTLA-4 antibody or isotype control, the first antibody injection being 1, 3, 5 or 7 days after the second virus injection. Tumor progression is measured over time. Black round points represent tumor progression in mice treated with the virus and isotype control whereas grey square, triangle, diamond and hexagon shaped points represent tumor progression in mice treated with the virus and the anti-CTLA-4 antibody 1, 3, 5 and 7 days after the second virus injection.

As shown in FIG. 7, tumor growth is delayed in mice treated with the combination of virus and anti-CTLA-4 (100 µg/mice) as compared to that measured in mice treated with the oncolytic virus and the isotype antibody. Tumor growth was even more delayed with short time period (day 1, 3 or 5 days) between the virus administrations and the antibody administrations with statistical differences observed for these 3 groups with respect to the control group at 6, 9 and 13 days post treatment. The same tendency was observed in the D+1, D+3 and D+5 groups of animals treated with the combination of WRTG17137 ($1\times10^7$ pfu/mice) and anti-CTLA-4 (50 µg/mice), although without any statistical differences with respect to the control group ($1\times10^7$ pfu/mice+100 µg isotype/mice).

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

The invention claimed is:

1. A method for treating a cancer, comprising administering:
   i) an oncolytic vaccinia virus, wherein said oncolytic vaccinia virus is defective for thymidine kinase (TK) resulting from inactivating mutations in the J2R viral gene and is defective for Ribonucleotide reductase (RR) activity resulting from inactivating mutations in the viral I4L and/or F4L gene(s) and
   ii) one or more immune checkpoint modulator(s) consisting of an antibody, wherein the antibody specifically binds to PD-1 and is selected from Nivolumab and Pembrolizumab,
   wherein said cancer is selected from the group consisting of: bone cancer, liver cancer, pancreatic cancer, stomach cancer, colon cancer, cancer of the esophagus, oro-pharyngeal cancer, lung cancer, cancer of the head or neck, skin cancer, melanoma, uterine cancer, cervix cancer, ovarian cancer, breast cancer, rectal cancer, cancer of the anal region, prostate cancer, lymphoma, cancer of the endocrine system, cancer of the thyroid gland, sarcoma of soft tissue, chronic or acute leukemias, cancer of the bladder, renal cancer, neoplasm of the central nervous system (CNS), and glioma,
   wherein said oncolytic vaccinia virus and said one or more immune checkpoint modulator(s) are administered sequentially and
   wherein said oncolytic vaccinia virus is administered first and said immune checkpoint modulator(s) is administered second.

2. The method of claim 1, wherein said oncolytic vaccinia virus further expresses at least one therapeutic gene inserted in the viral genome, wherein said therapeutic gene is selected from the group consisting of genes encoding suicide gene products and genes encoding immunostimulatory proteins.

3. The method of claim 2, wherein said suicide gene is selected from the group consisting of genes encoding a protein having a cytosine deaminase (CDase) activity, a thymidine kinase activity, an uracil phosphoribosyl transferase (UPRTase) activity, a purine nucleoside phosphorylase activity and a thymidylate kinase activity.

4. The method of claim 3, wherein said suicide gene product has CDase and UPRTase activities.

5. The method of claim 4, wherein said oncolytic vaccinia virus is defective for both TK and RR activities and comprising inserted into its genome the therapeutic FCU1 suicide gene.

6. The method of claim 2, wherein said immunostimulatory protein is an interleukin or a colony-stimulating factor.

7. The method of claim 6, wherein said oncolytic vaccinia virus is defective for TK activity and comprises inserted into its genome the therapeutic human GM-CSF.

8. The method according to claim 1 comprising from approximately $10^7$ pfu to approximately $5 \times 10^9$ pfu of said oncolytic vaccinia virus.

9. The method of claim 1, comprising from about 2 mg/kg to about 15 mg/kg of said one or more immune checkpoint modulator(s).

10. The method of claim 1, wherein said immune checkpoint modulator(s) is administered by intravenous, intratumoral or intraperitoneal route and wherein said oncolytic vaccinia virus is administered by intravenous or intratumoral route.

11. The method of claim 1, which comprises from 2 to 5 intravenous or intratumoral administrations of $10^8$ or $10^9$ pfu of oncolytic vaccinia virus at approximately 1 or 2 weeks interval followed by or interspersed with 2 to 5 intravenous administrations of 3 to 10 mg/kg of one or more anti-immune checkpoint antibody(ies)(s) every 2 or 3 weeks.

12. A kit comprising:
   i) in one container an oncolytic vaccinia virus, wherein said oncolytic vaccinia virus is defective for thymidine kinase (TK) resulting from inactivating mutations in the J2R viral gene and is defective for Ribonucleotide reductase (RR) activity resulting from inactivating mutations in the viral I4L and/or F4L gene(s);
   ii) in another container one or more immune checkpoint modulator(s) consisting of an antibody, wherein the antibody specifically binds to PD-1 and is selected from Nivolumab and Pembrolizumab; and
   iii) instructions for use indicating that said oncolytic vaccinia virus and said one or more immune checkpoint modulator(s) are to be administered sequentially and that said oncolytic vaccinia virus is to be administered first and said immune checkpoint modulator(s) is to be administered second.

13. A pharmaceutical composition comprising:
   i) an oncolytic vaccinia virus, wherein said oncolytic vaccinia virus is defective for thymidine kinase (TK) resulting from inactivating mutations in the J2R viral gene and is defective for Ribonucleotide reductase (RR) activity resulting from inactivating mutations in the viral I4L and/or F4L gene(s); and
   ii) one or more immune checkpoint modulator(s) consisting of an antibody, wherein the antibody specifically binds to PD-1 and is selected from Nivolumab and Pembrolizumab.

14. A method for treating a cancer, comprising administering:
   i) an oncolytic vaccinia virus, wherein said oncolytic vaccinia virus is defective for thymidine kinase (TK) resulting from inactivating mutations in the J2R viral gene and is defective for Ribonucleotide reductase (RR) activity resulting from inactivating mutations in the viral I4L and/or F4L gene(s), and wherein said oncolytic vaccinia virus is approximately $10^7$ pfu to approximately $5 \times 10^9$ pfu; and
   ii) an antibody selected from Nivolumab and Pembrolizumab, wherein said antibody is about 1 mg/kg to about 20 mg/kg;
   wherein said cancer is selected from the group consisting of: bone cancer, liver cancer, pancreatic cancer, stomach cancer, colon cancer, cancer of the esophagus, oro-pharyngeal cancer, lung cancer, cancer of the head or neck, skin cancer, melanoma, uterine cancer, cervix cancer, ovarian cancer, breast cancer, rectal cancer, cancer of the anal region, prostate cancer, lymphoma, cancer of the endocrine system, cancer of the thyroid gland, sarcoma of soft tissue, chronic or acute leukemias, cancer of the bladder, renal cancer, neoplasm of the central nervous system (CNS), and glioma;
   wherein said oncolytic vaccinia virus and said antibody are administered sequentially; and
   wherein said oncolytic vaccinia virus is administered first and said antibody is administered second.

* * * * *